(12) United States Patent
Blume et al.

(10) Patent No.: US 7,196,202 B2
(45) Date of Patent: Mar. 27, 2007

(54) 1-ARYL-2-N-, S- OR O-SUBSTITUTED BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

(75) Inventors: Thorsten Blume, Schildow (DE); Wolfgang Halfbrodt, Berlin (DE); Joachim Kuhnke, Potsdam (DE); Ursula Monning, Woltersdorf (DE); Herbert Schneider, Berlin (DE)

(73) Assignee: Schering AG, Berlin (DE)

( * ) Notice: Subject to any disclaimer, the term of this patent is extended or adjusted under 35 U.S.C. 154(b) by 205 days.

(21) Appl. No.: 11/066,015

(22) Filed: Feb. 24, 2005

(65) Prior Publication Data

US 2005/0143439 A1    Jun. 30, 2005

Related U.S. Application Data

(62) Division of application No. 10/190,620, filed on Jul. 9, 2002, now Pat. No. 6,903,126.

(60) Provisional application No. 60/304,124, filed on Jul. 11, 2001.

(30) Foreign Application Priority Data

Jul. 9, 2001    (DE) ............... 101 35 050

(51) Int. Cl.
  *C07D 235/30* (2006.01)
  *C07D 235/26* (2006.01)
(52) U.S. Cl. ............... 548/306.4; 548/307.4
(58) Field of Classification Search ............ 548/306.4, 548/307.4
  See application file for complete search history.

(56) References Cited

U.S. PATENT DOCUMENTS 4,520,196 A    5/1985  Wei
5,039,806 A    8/1991  Brandstram et al.
5,210,091 A    5/1993  Axelsson et al.
5,552,426 A    9/1996  Lunn et al.

FOREIGN PATENT DOCUMENTS

| DE | 19816915 | 10/1999 |
|---|---|---|
| DE | 199 00355 | 7/2000 |
| EP | 0 251536 | 1/1988 |
| EP | 0 419210 | 3/1991 |
| EP | 0 531883 | 3/1993 |
| EP | 0 604353 | 6/1994 |
| JP | 2000026430 | 1/2000 |
| WO | WO 95 07263 | 3/1995 |
| WO | WO 97 10219 | 3/1997 |
| WO | WO 00 59886 | 10/2000 |
| WO | WO 01 00213 | 1/2001 |
| WO | WO 01 47883 | 7/2001 |
| WO | WO 01 51473 | 7/2001 |

*Primary Examiner*—Laura L. Stockton
(74) *Attorney, Agent, or Firm*—Berlex, Inc.

(57) ABSTRACT

The invention relates to novel benzimidazole derivatives with general formula I, whereby radicals $R^1$, $R^2$, $R^3$, A, B, Y and Z have the meanings that are indicated in the description and the claims, the use of these compounds for the production of a pharmaceutical agent for treatment and prevention of diseases associated with microglia activation as well as pharmaceutical preparations that contain these compounds

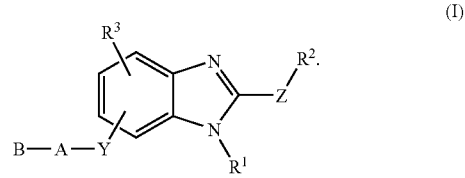

14 Claims, No Drawings

1-ARYL-2-N-, S- OR O-SUBSTITUTED BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

This application is a division of U.S. Ser. No. 10/190,620, filed Jul. 9, 2002, now U.S. Pat. No. 6,903,126, which claims priority to U.S. Provisional Application Ser. No. 60/304,124 filed Jul. 11, 2001 and German Application No. 10135050.3 filed Jul. 9, 2001.

The invention relates to new benzimidazole derivatives and the use of benzimidazole derivatives for the production of pharmaceutical agents for treatment and prevention of diseases that are associated with a microglia activation as well as pharmaceutical preparations that contain the new benzimidazole derivatives.

Almost all degenerative diseases of the central nervous system are associated with chronic inflammation. A central step of the inflammation process is the activation of mononuclear phagocyte cells, the microglia. This is carried out in, for example, Alzheimer's disease by senile plaques, in Creutzfeldt-Jacob disease by a prion protein and in ischemic stroke by dead cells. The microglia can remain for a prolonged period in the activated state, in which they produce and secrete various inflammation factors, for example, reactive oxygen/nitrogen intermediate products, proteases, cytokines, complement factors and neurotoxins. The latter in turn produce neuronal dysfunction and degeneration.

To treat inflammations and arteriosclerosis, i.a., benzimidazole derivatives had been proposed as active ingredients:

For example, in EP 0 104 727 A1, benzimidazole derivatives are indicated that are not substituted in 1-position and have an alkyl group in 2-position. Substituents in the benzene ring of the derivatives are, i.a., pyridyloxy radicals, pyridylalkyl radicals, pyridylalkyloxy radicals and pyridyloxyalkanediyl radicals.

In WO 01/21634 A1, benzimidazole derivatives are also described that in 1-position an alkanediylamido group can be substituted with at least one substituted alkoxy, alkylamino, alkylsulfonyl and alkylsulfoxide radical; in 2-position, i.a., a substituted phenyl or heteroaryl radical can be substituted with at least one substituted alkoxy, alkylamrino, alkylsulfonyl and alkylsulfoxide radical; and on the anellated benzene ring, i.a., with at least one substituted alkoxy, alkylamino, alkylsulfonyl and alkylsulfoxide radical. It is indicated that these substances can be used for a considerable number of possible indications as active ingredients in pharmaceutical agent preparations.

In U.S. Pat. No. 5,552,426, substituted benzimidazoles are indicated that have in 1-position, i.a., a phenyl or naphthyl radical, and in 2-position, i.a., a phenyl or heterocyclic radical. The anellated benzene ring of the benzimidazoles is preferably substituted with an alkoxy or aminoalkoxy radical. An effectiveness against diseases is ascribed to such compounds that are based on a neurotoxicity that is associated with a β-amyloid-peptide.

In WO 97/12613 A1, various agents that have an anti-inflammatory action and an arteriosclerosis-prophylactic action are described. For example, benzimidazole derivatives are indicated as active ingredients that are substituted in 1-position, i.a., with a phenyl radical or substituted phenyl radical and in 2-position with an alkoxy radical. Substituents in the benzene ring of the active ingredient compounds can be, i.a., alkyl, nitro, halo, alkoxy, amino, ester, amide, alkanediylalkoxy and alkanediylamino radicals.

In EP 0 520 200 A2, benzimidazole derivatives are indicated that have aryl radicals that are substituted in 1-position and amino groups that are monosubstituted or disubstituted in the 2-position or are unsubstituted. The benzene ring of the benzimidazole skeleton can be substituted with halogen, trifluoromethyl and/or cyano. These compounds are used to treat diseases that are associated with an increased activation of Ca channels.

In WO 97/33873 A1, benzimidazole derivatives are also indicated that are used to treat cystitis. These compounds can have in 1-position, i.a., phenyl, naphthyl and unsaturated heterocyclic radicals. In 2-position, the derivatives can be substituted with alkoxy, phenylalkoxy, naphthylalkoxy, heterocyclic alkoxy radicals or unsaturated heterocyclic alkoxy radicals. The benzene ring of the skeleton of the derivatives can be substituted with nitro, alkanoyl, amino, alkyl, alkoxy, cycloalkyl, heterocyclic, unsaturated heterocyclic, halo, alkylthio, hydroxyalkylidenyl, hydroxyalkylidenylamino, aminoalkylidenyl, aminoalkoxy, hydroxyalkyl, heterocyclic alkoxy, aminoalkylidenyl or trifluoromethyl radicals.

In EP 0 531 833 A1, condensed 5-membered heterocycles are indicated, for example substituted benzimidazole derivatives, whereby these compounds according to the general description of the compounds are preferably substituted in 1-position with a substituted alkyl radical and in 2-position, for example, with an O-alkanediyl, S-alkanediyl, NH-alkanediyl, N(alkyl)-alkanediyl, SO-alkanediyl or $SO_2$-alkanediyl radical. The anellated benzene ring can then be substituted, i.a., with an alkylenoxy, alkylenamino or alkylenamido group with a terminal carboxyl group. Preferably included are those compounds that are unsubstituted in the 1-position or that carry an alkyl group. In the very numerous examples, however, only compounds that carry an aryl or heterocyclic radical, especially a phenyl radical or an alkyl radical, in 1-position, are mentioned. The described compounds are to have an antithrombic action.

In the publications indicated above, it is only indicated that the described active ingredients are suitable for treating thromboses, arteriosclerosis, cystitis and diseases that are associated with a β-amyloid-peptide and with an increased activation of Ca-channels. An effect of the benzimidazole derivatives on microglia is not known from the documents, however.

For a possible treatment of neuroinflammation, to date non-steroidal anti-inflammatory agents (COX II inhibitors) [McGeer, P. L.; Roger, Neurology, 42, 447–449 (1992), Rogers, J.; Kirby, L. C.; Hempleman, S. R.; Berry, D. L.; McGeer, P. L.; Kaszniak, A. W.; Zalinski, J.; Cofield, M.; Mansukhani, L.; Wilson, P.; Kogan, F., Neurology, 43, 1609–1611 (1993), Andersen, K.; Launer, L. J.; Ott, A.; Hoes, A. W.; Breteler, M. M. B.; Hofman, A., Neurology, 45, 1441–1445 (1995), Breitner, J. C. S.; Gau, B. A.; Welsh, K. A.; Plassman, B. L.; McDonald, W. M.; Helms, M. J.; Anthony, J. C., Neurology, 44, 227–232 (1994), The Canadian Study of Health and Aging, Neurology, 44, 2073–2079 (1994)], cytokine modulators [McGeer, P. L., McGeer, E. G. Brain Res. Rev., 21:195–218 (1995), McGeer, E. G.; McGeer, P. L., CNS Drugs, 7, 214–228 (1997), Barone, F. C. and Feuerstein, G. Z., J. Cerebral Blood Flow and Metabolism, 19, 819–834 (1999)] and complement-cascade-inhibitors (Chen., S.; Frederickson, R. C. A., and Brunden, K. R., Neurobiol. Aging (1996), McGeer, E. G.; McGeer, P. L., Drugs, 55: 739–746 (1998)] have been described.

This invention is based on the problem that the known substances inhibit the synthesis or the action of individual inflammation factors without, however, the inflammation process being inhibited in an earlier step. The object therefore consists of finding substances that inhibit an earlier step in the inflammation process and thus prevent the development or the action of many inflammation factors.

The problem is solved by novel benzimidazole derivatives according to claim 1, in addition by a use of the benzimidazole derivatives according to the invention for the production of pharmaceutical agents for treatment of diseases that are associated with microglia activation and for prevention of these diseases as well as pharmaceutical preparations that contain the benzimidazole derivatives according to the invention.

The benzimidazole derivatives according to the invention have the following general structural formula I:

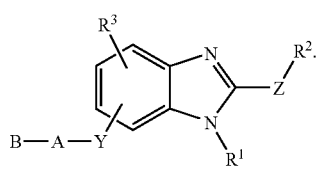

(I)

Here:

$R^1$ is an aryl group or a five- or six-membered heteroaryl group with one or two heteroatoms, selected from the group that comprises N, S and O, whereby the aryl group or heteroaryl group can be substituted with up to three radicals, independently of one another, selected from the group that comprises:

F, Cl, Br, $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$,

X—OH, X—$OR^4$, X—$OCOR^4$, X—$OCONHR^4$,

X—$COR^4$, X—$C(NOH)R^4$,

X—CN, X—COOH, X—$COOR^4$, X—$CONH_2$, X—$CONR^4R^{4'}$, X—$CONHR^4$,

X—CONHOH,

X—$SR^4$, X—$SOR^4$, X—$SO_2R^4$, $SO_2NH_2$, $SO_2NHR^4$, $SO_2NR^4R^{4'}$, $NO_2$, X—$NH_2$, X—$NHR^4$, X—$NR^4R^{4'}$, X—$NHSO_2R^4$, X—$NR^4SO_2R^{4'}$,

X—$NHCOR^4$, X—$NHCOOR^4$, X—$NHCONHR^4$ and $R^4$, whereby X is a bond, $CH_2$, $(CH_2)_2$ or $CH(CH_3)$, whereby also radicals $R^4$ and $R^{4'}$ are selected independently of one another according to the meanings that are further indicated below, and whereby two substituents at $R^1$, if they are in ortho-position to one another, are linked to one another in such a way that they jointly form a methanediyl-bisoxy, ethane-1,2-diylbisoxy, propane-1,3-diyl or butane-1,4-diyl group, Z is NH, $NR^{2'}$, O, S, SO or $SO_2$, whereby $R^{2'}$ has the meaning that is indicated below, $R^2$ and $R^{2'}$, independently of one another, in each case are a radical that is selected from the group that comprises:

$C_{1-4}$-perfluoroalkyl, $C_{1-6}$-alkyl, ($C_{0-3}$-alkanediyl-$C_{3-7}$ cycloalkyl), ($C_{0-3}$-alkanediyl-aryl) and ($C_{0-3}$-alkanediyl-heteroaryl), whereby the heteroaryl group is five- or six-membered and contains one or two heteroatoms, selected from the group that comprises N, S and O, and whereby the aryl and heteroaryl group in each case can be substituted with up to two radicals, selected from the group that comprises F, Cl, Br, $CH_3$, $C_2H_5$, OH, $OCH_3$, $OC_2H_5$, $NO_2$, $CF_3$, $C_2F_5$ and $SO_2NH_2$ and/or also can carry an anellated methanediylbisoxy group or ethane-1,2-diylbisoxy group, and in addition a ring member in a five-membered cycloalkyl ring can be ring-N or ring-O, and one or two ring members in a six- or seven-membered cycloalkyl ring can be ring-N and/or ring-O atoms, whereby the ring-N atoms optionally can be substituted with $C_{1-3}$-alkyl or $C_{1-3}$-alkanoyl, or if Z is $NR^{2'}$, $R^2$ and $R^{2'}$ together with Z form a five- to seven-membered heterocyclic ring, whereby the heterocyclic ring also can contain another N, O or S atom, and optionally can be substituted with a radical that is selected from the group that comprises $C_{1-4}$alkyl, ($C_{0-3}$-alkanediyl-$C_{1-3}$-alkoxy), $C_{1-4}$-alkanoyl, $C_{1-4}$-alkoxycarbonyl, aminocarbonyl and aryl, $R^3$ independently of one another, are one or two radicals, selected from the group that comprises:

hydrogen,

F, Cl, Br,

OH, $OR^4$, $OCOR^4$, $OCONHR^4$, $COR^4$,

CN, COOH, $COOR^4$, $CONH_2$, $CONHR^4$, $CONR^4R^{4'}$, CONHOH, $CONHOR^4$, $SR^4$, $SOR^4$, $SO_2R^4$, $SO_2NH_2$, $SO_2NHR^4$, $SO_2NR^4R^{4'}$, $NO_2$, $NH_2$, $NHR4$,$NR^4R^{4'}$, $NHSO_2R^4$, $NR^4SO_2R^{4'}$, $NHSO_2R^6$, $NR^4SO_2R^6$, $NHCOR^4$, $NHCOOR^4$, $NHCONHR^4$ and $R^4$, whereby radicals $R^4$, $R^{4'}$ and $R^6$ are selected independently of one another according to the meanings that are further indicated below, A is a group that is selected from the group that comprises $C_{1-10}$-alkanediyl, $C_{2-10}$-alkenediyl, $C_{2-10}$-alkinediyl and ($C_{0-3}$-alkanediyl-$C_{3-7}$-cycloalkanediyl-$C_{0-3}$-alkanediyl), whereby in a five-membered cycloalkyl ring, a ring member can be ring-N or ring-O and in a six- or seven-membered cycloalkyl ring, one or two ring members in each case can be ring-N and/or ring-O atoms, whereby the ring-N atoms optionally can be substituted with $C_{1-3}$-alkyl or $C_{1-3}$-alkanoyl, whereby in the above-mentioned aliphatic chains, a C atom can be exchanged for O, NH, N—$C_{1-3}$-alkyl or N—$C_{1-3}$-alkanoyl and whereby alkyl groups or cycloalkyl groups optionally can be substituted with a radical that is selected from the group that comprises =O, OH, O—$C_{1-3}$ alkyl, $NH_2$, NH—$C_{1-3}$-alkyl, NH—$C_{1-3}$-alkanoyl, $N(C_{1-3}$-alkyl$)_2$ and $N(C_{1-3}$-alkyl$)(C_{1-3}$-alkanoyl), B is a radical that is selected from the group that comprises COOH, $COOR^5$, $CONH_2$, $CONHNH_2$, $CONHR^5$, $CONR^5R^{5'}$, CONHOH, $CONHOR^5$ and tetrazolyl, in each case bonded to a C atom of group A, whereby radicals $R^5$ and $R^{5'}$, independently of one another, are selected according to the meanings that are further indicated below, Y is a group that is selected from the group that comprises O, NH, $NR^4$, $NCOR^4$, $NSO_2R^4$ and $NSO_2R^6$, whereby $R^4$ and $R^6$ have the meanings that are further indicated below, in which in the above radicals, radicals $R^4$, $R^{4'}$, $R^5$, $R^{5'}$ and $R^6$ have the following meanings; here:

$R^4$ and $R^{4'}$, independently of one another, in each case are a radical that is selected from the group that comprises $CF_3$, $C_2F_5$, $C_{1-4}$-alkyl, $C_{2-4}$-alkenyl, $C_{2-3}$-alkinyl and ($C_{0-3}$-alkanediyl-$C_{3-7}$-cycloalkyl), whereby in a five-membered cycloalkyl ring, a ring member can be ring-N or ring-O, and in a six- or seven-membered cycloalkyl ring, one or two ring members can be ring-N and/or ring-O atoms in each case, whereby the ring-N atoms optionally can be substituted with $C_{1-3}$-alkyl or $C_{1-3}$-alkanoyl, $R^5$ and $R^{5'}$, independently of one another, in each case are a radical that is selected from the group that comprises $C_{1-6}$-alkyl, $C_{2-6}$-alkenyl, $C_{2-6}$-alkinyl, whereby a C atom can be exchanged for O, S, SO, $SO_2$, NH, N—$C_{1-3}$-alkyl or N—$C_{1-3}$-alkanoyl, also ($C_{0-3}$-alkanediyl-$C_{3-7}$-cycloalkyl), whereby in a five-membered cycloalkyl ring, a ring member can be ring-N or ring-O and in a six- or seven-membered cycloalkyl ring, one or two ring members in each case can be ring-N and/or ring-O atoms, whereby the ring-N atoms optionally can be substituted with $C_{1-3}$-alkyl or $C_{1-3}$-alkanoyl, and also ($C_{0-3}$-alkanediyl-aryl) and ($C_{0-3}$-alkanediyl-heteroaryl), whereby the heteroaryl group is five- or six-membered and contains one or two heteroatoms, selected from the group that comprises N, S and O, whereby all previously mentioned alkyl and cycloalkyl radicals with up to two radicals, selected from the group that comprises $CF_3$, $C_2F_5$, OH, O—$C_{1-3}$ alkyl, $NH_2$, NH—$C_{1-3}$ alkyl, NH—$C_{1-3}$-alkanoyl, $N(C_{1-3}$-alkyl$)_2$, $N(C_{1-3}$-alkyl$)(C_{1-3}$-alkanoyl), COOH, $CONH_2$ and COO—$C_{1-3}$-alkyl, and all previously mentioned aryl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or can also carry an anellated methanediylbisoxy- or ethane-1,2-diylbisoxy group, or $R^5$ and $R^{5'}$ together with the amide-N atom of B form a five- to seven-membered, saturated or unsaturated heterocyclic ring, which can contain another N or O or S atom, and which can be substituted with $C_{1-4}$-alkyl, ($C_{0-2}$-alkanediyl-$C_{1-4}$-alkoxy), $C_{1-4}$-alkoxycarbonyl, aminocarbonyl or aryl, $R^6$ is a radical that is selected from the group that comprises ($C_{0-3}$-alkanediyl-aryl) and ($C_{0-3}$-alkanediyl-heteroaryl), whereby the heteroaryl group is five- or six-membered and contains one or two heteroatoms, selected from the group that comprises N, S and O, and whereby the aryl and heteroaryl groups can be substituted with up to tnvo radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$, and $SO_2NH_2$ and/or can also carry an anellated methanediylbisoxy group or ethane-1,2-diylbisoxy group.

Preferred are those benzimidazole derivatives in which the substituent B-A-Y is bonded to the 6-position of the benzimidazole.

Preferred are also those benzimidazole derivatives in which Z has the meaning of NH, $NR^{2'}$, S, SO or $SO_2$.

This invention also comprises physiologically compatible salts as well as esters of the above-mentioned compounds, especially the acid salts of the nitrogen bases of the benzimidazole derivatives according to the invention, also the salts of carboxylic acids of the derivatives according to the invention with bases, as well as the esters of carboxylic acids of the derivatives as well as carboxylic acids that are derived from carboxylic acid derivatives, for example carboxylic acid amides.

The benzimidazole derivatives according to the invention can have a chiral center or several chiral centers, so that the compounds can occur in several isomeric forms. The compounds of formula I can also be present as tautomers, stereoisomers or geometric isomers. The invention also comprises all possible isomers, such as E- and Z-isomers, S- and R-enantiomers, diastereomers, racemates and mixtures of the same including the tautomeric compounds. All of these isomeric compounds are—unless expressly indicated otherwise in each case—components of this invention. The isomeric mixtures can be separated into enantiomers or E/Z-isomers according to commonly used methods, such as, for example, crystallization, chromatography or salt formation.

The heteroaryl groups that are contained in the benzimidazole compounds according to the invention are built up from five or six skeleton atoms and can contain one or two heteroatoms. Heteroatoms are oxygen (O), nitrogen (N) and sulfur (S). Examples of heteroaryl groups are pyrrolyl, thienyl, furanyl, imidazolyl, thiazolyl, isothiazolyl, oxazolyl, isoxazolyl, pyrazolyl, pyridyl, pyrimidinyl, pyrazinyl and pyridazinyl. If the heteroaryl groups are part of $R^1$ or $R^2$, the group is bonded via a C atom to the respective N atom of the benzimidazole skeleton or to substituent Z.

As aryl radicals, primarily the phenyl radicals, but also the naphthyl radicals are suitable. The aryl and heteroaryl radicals can be bonded in any way to the benzimidazole skeleton or to another group, for example as a 1- or 2-naphthyl, 2-, 3- or 4-pyridinyl, 2-thienyl, 3-thienyl, 3-furyl or 2-pyridiminyl.

Alkyl groups can be straight-chain or branched. Examples of alkyl groups are methyl, ethyl, n-propyl, iso-propyl, n-butyl, sec-butyl, tert-butyl, n-pentyl, sec-pentyl, tert-pentyl, neo-pentyl, n-hexyl, sec-hexyl, heptyl, octyl, nonyl, and decyl. The higher homologues also comprise respectively both the linear and the branched alkyl groups, thus, for example, 2-ethylhexyl for octyl and 3-propyl-hexyl for nonyl.

Perfluorinated alkyls are preferably $CF_3$ and $C_2F_5$.

Alkenyl groups can be straight-chain or branched. For example, vinyl, 2-propenyl, 1-propenyl, 2-butenyl, 1-butenyl, 1-methyl-1-propenyl, 2-methyl-2-propenyl and 3-methyl-2-propenyl are alkenyl radicals in terms of the invention.

Alkinyl groups can be straight-chain or branched. Examples of this are ethinyl, 1-propinyl, 2-propinyl, 1-butinyl and 2-butinyl.

Cycloalkyl groups are defined in each case preferably as cyclopropyl, cyclobutyl, cyclopentyl, cyclohexyl or cycloheptyl (corresponds to $C_{3-7}$-cycloalkyl).

As a saturated heterocyclic ring or as cycloalkyl with one or more heteroatoms, there can be mentioned, for example: piperidine, pyrrolidine, tetrahydrofuran, morpholine, piperazine, hexahydroazepine as well as 2,6-dimethyl-morpholine, N-phenyl-piperazine, methoxymethyl-pyrrolidine, whereby the linkage can be carried out with a C atom that is adjacent to the ring on optionally present ring-N atoms.

Alkanediyl, alkenediyl, alkinediyl and cycloalkanediyl radicals that are mentioned in the description of the invention are the same in meaning as alkylene, alkenylene, alkinylene and cycloalkylene. If in the general formulas of the alkanediyl radicals the number of the C atoms contained is indicated and the value 0 is indicated as a lower limit for the range of this number, this alkanediyl radical is not contained in the respective case.

As alkanes, alkenes and alkines for A, for example, the following are mentioned: straight-chain or branched alkanediyl with one to eight C atoms, for example, methanediyl, ethanediyl, propanediyl, butanediyl, pentanediyl, hexanediyl, also 1-methylethanediyl, 1-ethylethanediyl, 1-methylpropanediyl, 2-methylpropanediyl, 1-methylbutanediyl, 2-methylbutanediyl, 1-ethylbutanediyl, 2-ethylbutanediyl, 1-methylpentanediyl, 2-methylpentanediyl, 3-methylpentanediyl and analogous compounds.

Straight-chain or branched alkenediyl and alkinediyl with two to eight C atoms are alkenediyl groups or alkinediyl groups with double and triple bonds in all possible positions and with all possible methyl or ethyl substitutions. In these radicals, in each case one or two C atoms can be exchanged for O, NH, N—$C_{1-3}$-alkyl or N—$C_{1-3}$-alkanoyl, whereby the exchanged group is separated from Y by at least two C atoms.

If two radicals are in ortho-position, they can form a common ring with the adjacent aromatic compounds. Compounds in which N, O or S atoms are bonded to olefinic or acetylenic multiple bonds, or in which several N, O, S or halogen atoms are bonded to the same aliphatic C atom, or in which N, O or S atoms are bonded to one another directly, are excluded if these linkages are not defined explicitly, for example in the functional groups or in heteroaromatic compounds that are mentioned in the claim.

The physiologically compatible salts of the nitrogen bases of the benzimidazole derivatives according to the invention can be formed with inorganic and organic acids, for example with oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid, and methanesulfonic acid.

For salt formation of acid groups, especially carboxylic acid groups, inorganic or organic bases are also suitable that are known for the formation of physiologically compatible salts, such as, for example, alkali hydroxides, especially sodium and potassium hydroxide, alkaline-earth hydroxides, such as calcium hydroxide, also ammonia, as well as amines, such as ethanolamine, diethanolamine, triethanolamine, N-methylglucamine and tris-(hydroxymethyl)-methylamine.

For ester formation, all lower monovalent, divalent and trivalent alcohols are suitable, especially methanol, ethanol, iso-propanol and tert-butanol, as well as ethylene glycol and glycerol.

Preferred are benzimidazoles with general formula I, in which the radicals and groups that are indicated below, independently of one another, have the following meanings:

$R^1$ means a phenyl group, which can be substituted with up to two radicals, independently of one another, selected from the group that comprises:

F, Cl, Br,
C(NH)$NH_2$, C(NH)$NHR^4$, C(NH)$NR^4R^{4'}$, C($NR^4$)$NH_2$, C($NR^4$)$NHR^{4'}$,
C($NR^4$)$NR^4R^{4'}$,
OH, $OR^4$, $OCOR^4$, $OCONHR^4$,
$COR^4$, C(NOH)$R^4$,
CN, COOH, $COOR^4$, $CONH_2$, $CONR^4R^{4'}$, $CONHR^4$, CONHOH,
$SR^4$, $SOR^4$, $SO_2R^4$,
$SO_2NH_2$, $SO_2NHR^4$, $SO^2NR^4R^{4'}$,
$NO_2$, $NH_2$, $NHR^4$, $NR^4R^{4'}$, $NHCONHR^4$ and $R^4$, whereby radicals $R^4$ and $R^{4'}$ are selected independently of one another according to meanings that are indicated below and whereby two substituents at $R^1$ are linked to one another in such a way that they jointly form a methanediylbisoxy, ethane-1,2-diylbisoxy, propane-1,3-diyl or butane-1,4-diyl group, if they are in ortho-position to one another, Z has the same meaning as indicated above, $R^2$ and $R^{2'}$ have the same meanings as indicated above, $R^3$ means a radical that is selected from the group that comprises hydrogen, F, Cl, Br, $CH_3$, $C_2H_5$, $CF_3$, $C_2F_5$, OH, $OR^4$, $NHSO_2R^6$ and $NHCOR^4$, whereby $R^4$ and $R^6$ have the meanings that are further indicated below, A has the same meaning as indicated above, B means a radical that is selected from the group that comprises COOH, $COOR^5$, $CONH_2$, $CONHR^5$ and $CONR^5R^{5'}$, in each case bonded to a C atom of group A, whereby radicals $R^5$ and $R^{5'}$ are selected independently of one another according to the meanings that are further indicated above, Y means O, in which in the above radicals, radicals $R^4$, $R^{4'}$, $R^5$, $R^{5'}$ and $R^6$ have the following meanings; here:

$R^4$ and $R^{4'}$ have the same meanings as indicated above, $R^5$ and $R^{5'}$, independently of one another, in each case mean a radical that is selected from the group that comprises $C_{1-6}$alkyl, $C_{2-6}$-alkenyl, $C_{2-6}$-alkinyl, whereby a C atom can be exchanged for O, S, SO, $SO_2$, NH, N—$C_{1-3}$-alkyl or N—$C_{1-3}$-alkanoyl, also ($C_{0-3}$-alkanediyl-$C_{3-7}$-cycloalkyl), whereby in a five-membered cycloalkyl ring, a ring member can be ring-N or ring-O and in a six- or seven-membered cycloalkyl ring, one or two ring members in each case can be ring-N atoms and/or ring-O atoms, whereby the ring-N atoms optionally can be substituted with $C_{1-3}$-alkyl or $C_{1-3}$-alkanoyl, and also ($C_{0-3}$-alkanediyl-phenyl) and ($C_{0-3}$-alkanediyl-heteroaryl), whereby the heteroaryl group is five- or six-membered and contains one or two heteroatoms, selected from the group that comprises N, S and O, whereby all previously mentioned alkyl and cycloalkyl radicals can be substituted with a radical that is selected from the group that comprises $CF_3$, $C_2F_5$, OH, O—$C_{1-3}$ alkyl, $NH_2$, NH—$C_{1-3}$-alkyl, NH—$C_{1-3}$-alkanoyl, N($C_{1-3}$-alkyl)$_2$, N($C_{1-3}$-alkyl)($C_{1-3}$-alkanoyl), COOH, $CONH_2$ and COO—$C_{1-3}$ alkyl, and all previously mentioned phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or also can carry an anellated methanediylbisoxy group or ethane-1,2-diylbisoxy group, or $R^5$ and $R^{5'}$ together with the amide-N atom of B form a five- to seven-membered, saturated or unsaturated heterocyclic ring, which can contain another N or O or S atom and which can be substituted with $C_{1-4}$-alkyl, ($C_{0-2}$-alkanediyl-$C_{1-4}$-alkoxy), $C_{1-4}$-alkoxycarbonyl, aminocarbonyl or phenyl, $R^6$ means a phenyl or heteroaryl group, whereby the heteroaryl group is five- or six-membered and contains one or two heteroatoms, selected from the group that comprises N, S and O, and whereby the phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, CF$_3$, C$_2$F$_5$ and SO$_2$NH$_2$, or else can carry an anellated methanediylbisoxy group or ethane-1,2-diylbisoxy group.

Especially preferred are benzimidazoles with general formula I, in which the radicals and groups that are indicated below, independently of one another, have the following meanings:

R$^1$ means a phenyl group, which can be substituted with up to two radicals, independently of one another, selected from the group that comprises:
F, Cl, Br,
C(NH)NH$_2$, C(NH)NHR$^4$, C(NH)NR$^4$R$^{4'}$, C(NR$^4$)NH$_2$, C(NR$^4$)NHR$^{4'}$,
C(NR$^4$)NR$^4$R$^{4'}$,
OH, OR$^4$, OCOR$^4$, OCONHR$^4$,
COR$^4$, C(NOH)R$^4$,
CN, COOH, COOR$^4$, CONH$_2$, CONR$^4$R$^{4'}$, CONHR$^4$, CONHOH,
SR$^4$, SOR$^4$, SO$_2$R$^4$,
SO$_2$NH$_2$, SO$_2$NHR$^4$, SO$^2$NR$^4$R$^{4'}$,
NO$_2$, NH$_2$, NHR$^4$, NR$^4$R$^{4'}$, NHCONHR$^4$ and R$^4$,
whereby radicals R$^4$ and R$^{4'}$ are selected independently of one another according to meanings that are indicated below and whereby two substituents at R$^1$ are linked to one another in such a way that they jointly form a methanediylbisoxy, ethane-1,2-diylbisoxy, propane-1,3-diyl or butane-1,4-diyl group, if they are in ortho-position to one another, Z has the same meaning as indicated above, R$^2$ and R$^{2'}$, independently of one another, in each case mean a radical that is selected from the group that comprises:
C$_{1-4}$-perfluoroalkyl, C$_{1-5}$-alkyl, (C$_{0-3}$-alkanediyl-aryl) and (C$_{0-3}$-alkanediyl-heteroaryl),
whereby the heteroaryl group is five- or six-membered and contains one or two heteroatoms, selected from the group that comprises N, S and O, and whereby the aryl and heteroaryl group in each case can be substituted with up to two radicals, selected from the group that comprises F, Cl, Br, CH$_3$, C$_2$H$_5$, OH, OCH$_3$, OC$_2$H$_5$, NO$_2$, CF$_3$, C$_2$F$_5$ and SO$_2$NH$_2$,
or if Z is NR$^{2'}$, R$^2$ and R$^{2'}$ together with Z form a five- to seven-membered heterocyclic ring, whereby also the heterocyclic ring can contain an additional O or S atom and optionally can be substituted with a radical that is selected from the group that comprises C$_{1-4}$-alkyl, (C$_{0-3}$-alkanediyl-C$_{1-3}$-alkoxy), C$_{1-4}$-alkanoyl, C$_{1-4}$-alkoxycarbonyl, aminocarbonyl and aryl, R$^3$ means hydrogen, A means straight-chain or branched alkanediyl with up to 8 C atoms, B means a radical that is selected from the group that comprises COOH, COOR$^5$, CONH$_2$, CONHR$^5$ and CONR$^5$R$^{5'}$, in each case bonded to a C atom of group A, whereby radicals R$^5$ and R$^{5'}$ are selected independently of one another according to the meanings that are further indicated below, Y means O, in which in the above radicals, radicals R$^4$, R$^{4'}$, R$^5$, and R$^{5'}$ have the following meanings; here:

R$^4$ and R$^{4'}$, independently of one another, in each case mean a radical that is selected from
the group that comprises CF$_3$, C$_2$F$_5$, C$_{1-4}$-alkyl, C$_{2-4}$-alkenyl, C$_{2-3}$-alkinyl and (C$_{0-3}$-alkanediyl-C$_{3-7}$-cycloalkyl),
whereby alkyl radicals optionally can be substituted with a radical that is selected from the group that comprises OH, OCH$_3$ and SCH$_3$, R$^5$ and R$^{5'}$, independently of one another, in each case mean a radical that is selected from the group that comprises C$_{1-6}$alkyl, C$_{2-6}$-alkenyl, C$_{2-6}$-alkinyl, (C$_{0-3}$-alkanediyl-C$_{3-7}$-cycloalkyl), (C$_{0-3}$-alkanediyl-phenyl) and (C$_{0-3}$-alkanediyl-heteroaryl), whereby the heteroaryl group is five- or six-membered and contains one or two heteroatoms, selected from the group that comprises N, S and O,
whereby all previously mentioned alkyl and cycloalkyl radicals can be substituted with a radical that is selected from the group that comprises CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, N(C$_{1-3}$-alkyl)(C$_{1-3}$-alkanoyl), COOH, CONH$_2$ and COO—C$_{1-3}$-alkyl, and all previously mentioned phenyl and heteroaryl groups can be substituted with up to two radicals, selected from the group that comprises F, Cl, Br, CH$_3$, C$_2$H$_5$, OH, OCH$_3$, OC$_2$H$_5$, NO$_2$, N(CH$_3$)$_2$, CF$_3$, C$_2$F$_5$ and SO$_2$NH$_2$, and/or also can carry an anellated methanediylbisoxy group or ethane-1,2-diylbisoxy group,
or R$^5$ and R$^{5'}$ together with the amide-N atom of B form a five- to seven-membered, saturated or unsaturated heterocyclic ring, which can contain another N or O or S atom and which can be substituted with C$_{1-4}$-alkyl, (C$_{0-2}$-alkanediyl-C$_{1-4}$-alkoxy), C$_{1-4}$-alkoxycarbonyl, aminocarbonyl or phenyl.

R$^1$ is especially phenyl or methylphenyl. R$^2$ can preferably be a radical that is selected from the group that comprises C$_{1-3}$-alkyl, phenyl, methylphenyl, methanediylphenyl and heteroaryl.

Z, together with R$^2$, can also form a saturated, 5- or 6-membered heterocyclic ring that can contain an additional O or S atom, such as, for example, a piperidine or morpholine ring.

R$^3$ is preferably hydrogen. The grouping Y-A is set forth in a preferred embodiment by an n-pentanedioxy group (—C$_5$H$_{10}$—O), which is bonded via the O atom to the benzimidazole skeleton. As an alternative, the groupings can also be used with shorter or longer alkanediyl radicals, for example n-butanediyloxy or n-hexanediyloxy.

Terminal group B preferably stands for COOH, COOR, whereby R in particular can be C$_{1-4}$-alkyl, such as methyl, ethyl, iso-propyl or tert-butyl, or an amide group, for example, a C$_{1-6}$-alkylamido group, whereby alkyl in particular can be iso-propyl or iso-butyl, a dialkylamido group, whereby alkyl in particular can be methyl, or a 3-alkoxypropanediyl-amino group, whereby alkoxy can be a methyloxy, iso-butyloxy or iso-pentyloxy group.

The structural features that are different from the individual derivatives are set forth in Table 2, whereby the indicated structural features relate to general formula II that is also indicated in the Table.

The benzimidazole derivatives according to the invention inhibit the activation of microglia. Microglia are defined here as the macrophages of the brain. The invention therefore also relates to the use of these derivatives for the production of pharmaceutical agents for treating diseases that are associated with a microglia activation as well as for preventing the diseases. In this case, a corresponding use of such derivatives is also included with general formula I, in which B stands for hydrogen, and in which radicals R$^1$, R$^2$, R$^3$, A, B, Y and Z have the above-indicated meanings. Other radicals R$^4$, R$^5$ and R$^6$ that also define these radicals or groups are also defined by the meanings that are further indicated above. In addition to the use of the new benzimidazole derivatives according to the invention for the production of the above-mentioned pharmaceutical agents, the invention also relates to a corresponding use of benzimidazole derivatives, in which B stands for hydrogen. The use of these derivatives, which are used as components for pharmaceutical agents for treating diseases that are associated with a microglia activation as well as for preventing these diseases, is new, even if these other compounds are not new themselves (U.S. Pat. No. 5,552,426).

The compounds of formula I inhibit the activation of the microglia and the production of interleukin 12 (IL 12) and interferon γ (INFγ). The invention therefore also relates to the use of a compound of formula I, as well as optical or geometric isomers thereof or tautomers or physiologically compatible salts thereof for the production of a pharmaceutical agent for treating or preventing a disease that is associated with a microglia activation as well as a disease that is triggered by over-production of IL 12 and IFNγ and for induction of interleukin 10 (IL-10).

Based on their ability to inhibit the activation of microglia and to interrupt the production of IL 12 and TNFα in monocytes/macrophages and the INFγ production in T cells and NK cells and to increase the induction of the IL-10 production, the compounds according to the invention are suitable for treating numerous diseases that are triggered by the intensified production of cytokines, such as, e.g., TNFα, β, IFNγ, IL 2 and IL12, such as inflammatory diseases, autoimmune diseases, allergic and infectious diseases, toxin-induced inflammations, pharmacologically triggered inflammation reactions as well as pathophysiologically relevant inflammation reactions of an origin that is as yet unclear.

Examples of inflammatory and autoimmune diseases are: chronic inflammatory intestinal diseases (inflammatory bowel diseases, Crohn's disease, ulcerative colitis), arthritis, allergic contact dermatitis, psoriasis, pemphigus, asthma, multiple sclerosis, diabetes, type I insulin-dependent diabetes mellitus, rheumatoid arthritis, lupus diseases and other collagenoses, Graves' disease, Hashimoto's disease, "graft-versus-host disease" and transplant rejections.

Examples of allergic, infectious and toxin-triggered and ischemia-triggered diseases are: sarcoidosis, asthma, hypersensitive pneumonitis, sepsis, septic shock, endotoxin shock, toxic shock syndrome, toxic liver failure, ARDS (acute respiratory distress syndrome), eclampsia, cachexia, acute viral infections (e.g., mononucleosis, fulminant hepatitis), and post-reperfusion organ damage.

An example of a pharmacologically triggered inflammation with pathophysiological relevance is the "first dose response" after administration of anti-T-cell antibodies such as OKT3.

An example of systemic inflammation reactions of an origin that is as yet unclear is eclampsia.

Examples of neuroinflammatory diseases that are associated with a microglia activation are AIDS dementia, amyotrophic lateral sclerosis, Creutzfeldt-Jakob disease, Down's syndrome, diffuse Lewy body disease, Huntington's disease, leukoencephalopathy, multiple sclerosis, Parkinson's disease, Pick's disease, Alzheimer's disease, stroke, temporary lobe epilepsy and tumors. The invention therefore also relates to the use of the indicated benzimidazole derivatives for treating these diseases as well as for preventing these diseases.

The action of the benzimidazole derivatives according to the invention in the treatment and prevention of microglia-associated diseases is surprising, since to date benzimidazole derivatives had been described only for the treatment of thromboses and arteriosclerosis [EP 0 531 883 A1, EP 0 104 727 A1, WO 97/12613 A1], cystitis [WO 97/33873 A1] and diseases that are associated with a β-amyloid peptide [U.S. Pat. No. 5,552,426] as well as an increased activation of Ca-channels [EP 0 520 200 A2], but an effect on microglia is not known.

Example 45 describes how the inhibition of the microglia activation can be measured. In this case, the activation of the microglia can be carried out by various stimuli, such as with, for example, Aβ-peptide [β-Amyloid, Araujo, D. M. and Cotman, C. M., *Brain Res.*, 569, 141–145 (1992)], with prion protein, cytokines or by cell fragments [Combs, C. K. et al., *J. Neurosci.*, 19, 928–939, (1999), Wood, P. L., Neuroinflammation: Mechanisms and Management, *Humana Press*, (1998)].

The stimulation with the Aβ-peptide corresponds to the pathophysiological situation in Alzheimer's disease. In this test, the substances according to the invention showed inhibition of microglia activation in the case of stimulation with the Aβ-peptide. The inhibition of the microglia activation by the substances according to the invention results in a strong reduction of the cytokine production and secretion, e.g., of Il1β and TNFα (measured by ELISA and mRNA expression analysis) and in a reduced secretion of reactive oxygen/nitrogen intermediate products. Several inflammation factors are thus equally inhibited.

The in-vivo effectiveness of the substances according to the invention is shown in an MCAO model in rats. This model simulates the condition of a stroke. The substances according to the invention reduce the microglia activation, which occurs in the case of acute cerebral lesions in the brains of animals.

The inhibition of cytokine production is represented, for example, by measuring TNFα and interleukin 12 in lipopolysaccharide (LPS)-stimulated THP-1 cells.

The compounds according to the invention inhibit the TNFα and interleukin 12 production in lipopolysaccharide (LPS)-stimulated THP-1 cells. To show the influence of the substances on the T-cell activation, for example, the measurement of the INFγ secretion is used. The compounds according to the invention inhibit the INFγ production of peripheral mononuclear blood cells.

The invention also relates to pharmaceutical agents that contain one or more compounds of general formula I according to the invention as well as one or more vehicles. The pharmaceutical agents or compositions of the invention are produced in a way that is known in the art with the commonly used solid or liquid vehicles or diluents and the commonly used pharmaceutical and technical adjuvants corresponding to the desired type of administration with a suitable dosage. The preferred preparations consist of a form for dispensing that is suitable for oral, enteral or parenteral, for example i.p. (intraperitoneal), i. v. (intravenous), i.m. (intramuscular) or percutaneous, administration. Such forms for dispensing are, for example, tablets, film tablets, coated tablets, pills, capsules, powders, creams, ointments, lotions, liquids, such as syrups, gels, injectable liquids, for example for i.p., i.v., i.m. or percutaneous injection, etc. In addition, depot forms, such as implantable preparations, as well as suppositories, are also suitable. In this case, depending on their type, the individual preparations release to the body the derivatives according to the invention gradually or all at once in a short time.

For oral administration, capsules, pills, tablets, coated tablets and liquids or other known oral forms for dispensing can be used as pharmaceutical preparations. In this case, the pharmaceutical agents can be formulated in the way that they release the active ingredients either in a short time and pass on to the body or have a depot action, so that a longer-lasting, slow supply of active ingredients to the body is achieved. In addition to at least one benzimidazole derivative, the dosage units can contain one or more pharmaceutically compatible vehicles, for example substances for adjusting the rheology of the pharmaceutical agent, surfactants, solubilizers, microcapsules, microparticles, granulates, diluents, binders, such as starches, sugar, sorbitol and gelatins, also fillers, such as silicic acid and talc, lubricants, dyes, perfumes and other substances.

Corresponding tablets can be obtained, for example, by mixing active ingredient with known adjuvants, for example inert diluents such as dextrose, sugar, sorbitol, mannitol, polyvinylpyrrolidone, explosives such as corn starch or alginic acid, binders such as starch or gelatin, lubricants such as carboxypolymethylene, carboxy methyl cellulose, cellulose acetate phthalate or polyvinyl acetate. The tablets can also consist of several layers.

Coated tablets can be produced accordingly by coating cores that are produced analogously to the tablets with agents that are commonly used in coated tablet coatings, for example polyvinylpyrrolidone or shellac, gum arabic, talc, titanium oxide or sugar. In this case, the shell of the coated tablet can also consist of several layers, whereby the adjuvants that are mentioned above in the case of the tablets can be used.

Capsules that contain active ingredients can be produced, for example, by the active ingredient being mixed with an inert vehicle such as lactose or sorbitol and encapsulated in gelatin capsules.

The benzimidazole derivatives according to the invention can also be formulated in the form of a solution, which is intended for oral administration and which in addition to the active benzimidazole derivative contains as components a pharmaceutically compatible oil and/or a pharmaceutically compatible lipophilic surfactant and/or a pharmaceutically compatible hydrophilic surfactant and/or a pharmaceutically compatible water-miscible solvent.

To achieve better bio-availability of the active ingredients according to the invention, the compounds can also be formulated as cyclodextrin clathrates. To this end, the compounds are reacted with α-, β- or γ-cyclodextrin or derivatives thereof.

If creams, ointments, lotions and liquids that can be applied topically are to be used, the latter must be constituted so that the compounds according to the invention are fed to the body in adequate amounts. In these forms for dispensing, adjuvants are contained, for example substances for adjusting the rheology of pharmaceutical agents, surfactants, preservatives, solubilizers, diluents, substances for increasing the permeability of the benzimidazole derivatives according to the invention through the skin, dyes, perfumes and skin protection agents, such as conditioners and moisturizers. Together with the compounds according to the invention, other active ingredients can also be contained in the pharmaceutical agent [*Ullmanns Enzyklopädie der technischen Chemie [Ullmanns' Encyclopedia of Technical Chemistry]*, Volume 4 (1953), pages 1–39; *J. Pharm. Sci.*, 52, 918 ff. (1963); issued by Czetsch-Lindenwald, *Hilfsstoffe für Pharmazie und angrenzende Gebiete [Adjuvants for Pharmaceutics and Related Fields]*; *Pharm. Ind.*, 2, 72 ff (1961); Dr. H. P. Fiedler, *Lexikon der Hiffsstoffe für Pharmazie, Kosmetik und angrenzende Gebiete [Dictionary of Adjuvants for Pharmaceutics, Cosmetics and Related Fields]*, Cantor AG, Aulendorf/Württ., 1971].

The substances according to the invention can also be used in suitable solutions such as, for example, physiological common salt solution, as infusion or injection solutions. For parenteral administration, the active ingredients can be dissolved or suspended in a physiologically compatible. diluent. As diluents, in particular oily solutions, such as, for example, solutions in sesame oil, castor oil and cottonseed oil, are suitable. To increase solubility, solubilizers, such as, for example, benzyl benzoate or benzyl alcohol, can be added.

To formulate an injectable preparation, any liquid vehicle can be used in which the compounds according to the invention are dissolved or emulsified. These liquids frequently also contain substances to regulate viscosity, surfactants, preservatives, solubilizers, diluents and other additives, with which the solution is set to isotonic. Other active ingredients can also be administered together with the benzimidazole derivatives.

It is also possible to incorporate the substances according to the invention in a transdermal system and thus to administer them transdermally. To this end, the benzimidazole derivatives are applied in the form of a depot injection or an implant preparation, for example subcutaneously. Such preparations can be formulated in such a way that a delayed release of active ingredients is made possible. To this end, known techniques can be used, for example depots that dissolve or operate with a membrane. Implants can contain as inert materials, for example, biodegradable polymers or synthetic silicones, for example silicone gum. The benzimidazole derivatives can also be incorporated in, for example, a patch, for percutaneous administration.

The dosage of the substances of general formula I according to the invention is determined by the attending physician and depends on, i.a., the substance that is administered, the method of administration, the disease that is to be treated and the severity of the disease. The daily dose is no more than 1000 mg, preferably no more than 100 mg, whereby the dose can be given as a single dose to be administered once or divided into two or more daily doses.

1-Aryl-2N—, —S— or —O-substituted benzimidazoles (G, H, K, L, N, P)—see diagrams 2 to 4—are accessible in various ways according to processes that are known in the literature per se.

As possible processes, in addition to others, the following can be mentioned:

By reaction of arylamines (B) with ortho-leaving group-substituted, preferably halogen-substituted nitrobenzene derivatives (A), N-aryl-2-nitrobenzenes (C) can be produced under various reaction conditions, such as, for example, by heating the reactants with or without a suitable inert solvent, such as, for example, alkyl or halo-benzenes. The amine that is used as reactant can also be used in excess as a solvent. The reactions are performed both without and with bases, for example potassium carbonate or sodium hydride. Other adjuvants, such as, for example, copper salts, are also used. Examples of the procedures that are indicated here are found in numerous works, such as, for example, in: D. Jerchel, H.Fischer, M. Graft, *Ann. Chem.* 575, 162 (1952), *CAS*, 53, (2138); R.-A. Abramovitch, *Can. J. Chem.*, 38, 2273 (1960).

The nitro group (C→D) is preferably reduced by hydrogenation in polar solvents, such as acetic acid, lower alcohols or ethyl acetates, with the addition of catalysts, such as Raney nickel or palladium on carbon, or by chemical reduction, for example with tin in hydrochloric acid, $SnCl_2$ [F. D. Bellamy, *Tet. Lett.* (1984)] or Fe/acetic acid [D. C. Owsily, J. J. Bloomfield, *Synthesis,* 118, 150 (1977)].

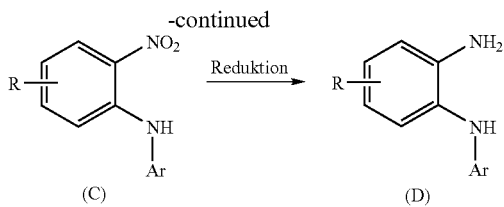

DIAGRAM 1

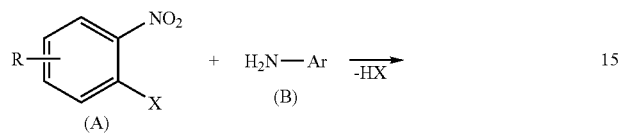

X = Abgangsgruppe
R = Substitueut(en) oder H

[Key:]
Reduktion = reduction
X = Abgangsgruppe = Leaving group
R = Substituent(en) oder H = Substituent(s) or H

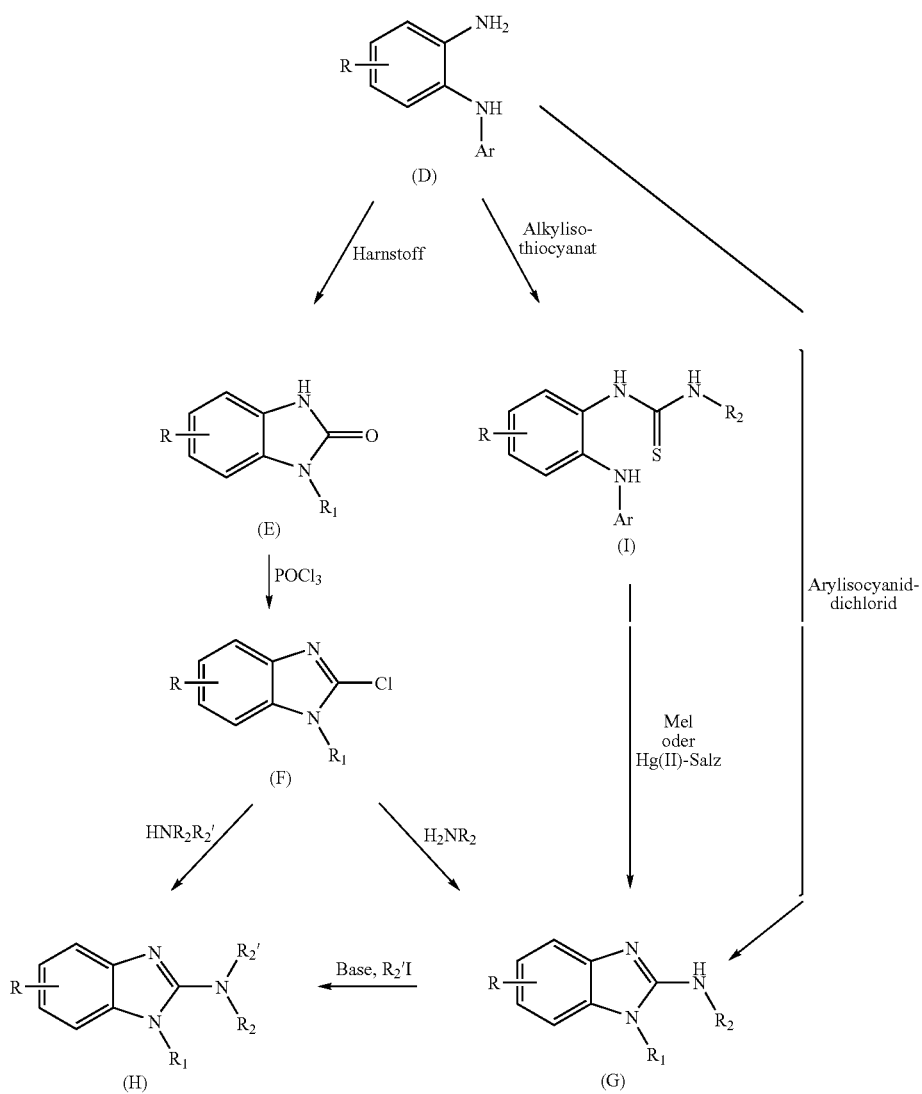

[Key:]
Harnstoff = urea
Alkylisothiocyanat = alkylisothiocyanate
Arylisocyanid-dichlorid = arylisocyanide-dichloride
MeI oder HG(II)-Salz = MeI or Hg(II) salt The thus obtained diaminobenzenes of type D can be converted in various ways to 1-aryl-2N—, —S— or —O-substituted benzimidazoles (G, H, K, L, N, P):

By reaction of diamines of type D with carboxylic acid derivatives, such as, for example, urea [H. Goeker, G. Ayhan-Kilcigil, M. Tuncbilek, C. Kus, R. Ertan, E. Kendi, S. Oezbey, M. Fort, C. Garcia, A. Farre, *J. Heterocycles*, 1999, 2561], benzimidazolones of type E can be produced, whose treatment with phosphorus oxychloride [M. J. Kukla, H. J. Breslin, C. J. Diamond, P. P. Grous, C. Y. Ho et al., *J. Med. Chem.*, 1991, 3187; J. Turner; *J. Chem. Soc.* 1950, 1515] yields 2-chlorobenzimidazoles of type F. The reaction of these benzimidazoles with primary or secondary amines [M. J. Kukla, H. J. Breslin, C. J. Diamond, P. P. Grous, C. Y. Ho et al., *J. Med. Chem.*, 1991, 3187; Efros et al., *Zh. Obshch. Khim.*, 1953, 1691; J. Turner, *J. Chem. Soc.*, 1950, 1515; Z. Zhu, B. Lippa, J. C. Drach, L. B. Townsend, *J. Med. Chem.*, 2000, 2430; H. Goeker, G. Ayhan-Kilcigil, M. Tuncbilek, C. Kus, R. Erlan, E. Kendi, S. Oezbey, M. Fort, C. Garcia, A. Farre, *J. Heterocycles*, 1999, 2561; J. Musco, D. B. Murphy, *J. Org. Chem.*, 1971, 3469] results in 2-amino-substituted benzimidazoles of types G and H. The benzimidazoles of type G can also be reacted to form benzimidazoles H by base-mediated alkylation [K. Kubo, Y. Kohara, E. Imamiya, Y. Sugiura, Y. Inada et al., *J. Med. Chem.*, 1993, 2182]. Benzimidazoles of type G are also accessible, for example, in that phenylenediamines of type D are reacted with alkyl- or arylisothiocyanates to form thiourea derivatives I, which accompany a cyclization to benzimidazoles G in the case of subsequent treatment with methyl iodide [M. J. Kukla, H. J. Breslin, C. J. Diamond, P. P. Grous, C. Y. Ho et al., *J. Med. Chem.*, 1991, 3187] or with mercury(II) salts [F. Merchan, J. Garin, V. Martinez, E. Melendez, *Synthesis*, 1982, 482; K. C. Nicolaou, J. I. Trujillo, B. Jandeleit, K. Chibale, M. Rosenfeld et al., *Bioorg. Med. Chem.*, 1998, 1185]. The reaction of phenylenediamines of type D with arylisocyanide dichlorides [J. Musco, D. B. Murphy, *J. Org. Chem.*, 1971, 3469] represents another access to benzimidazoles of type G.

DIAGRAM 3

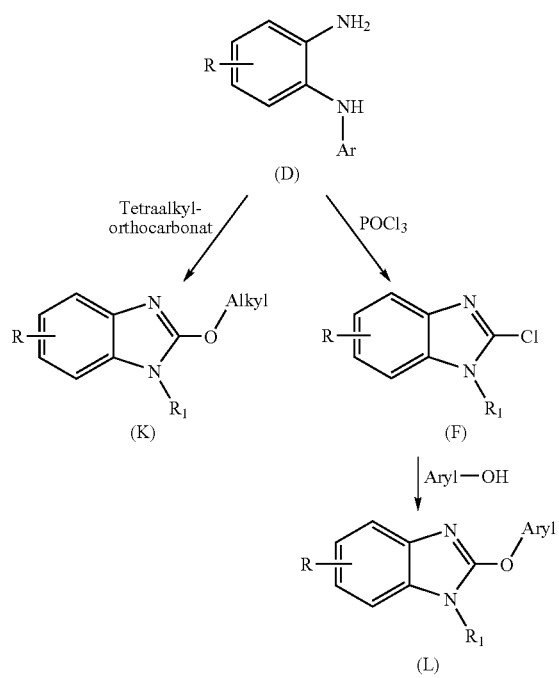

[Key:]
Tetraalkyl-orthocarbonat = tetraalkyl-orthocarbonate

From the diamines of type D, 2-alkoxybenzimidazoles (K) are accessible by, for example, reaction with tetraalkyl-orthocarbonates [M. J. Kukla, H. J. Breslin, C. J. Diamond, P. P. Grous, C. Y. Ho et al., *J. Med. Chem.*, 1991, 3187; Y. Abe, H. Kayakiri, S. Satoh, T. Inoue, Y. Sawada et al., *J. Med. Chem.*, 1998, 4062]. 2-Aryloxybenzimidazoles (L) can be produced by, for example, base-mediated reaction of phenols with 2-chlorobenzimidazoles (IF) [M. V. Kulkami, V. D. Patil., *Arch. Pharm.*, 1981; 440].

DIAGRAM 4

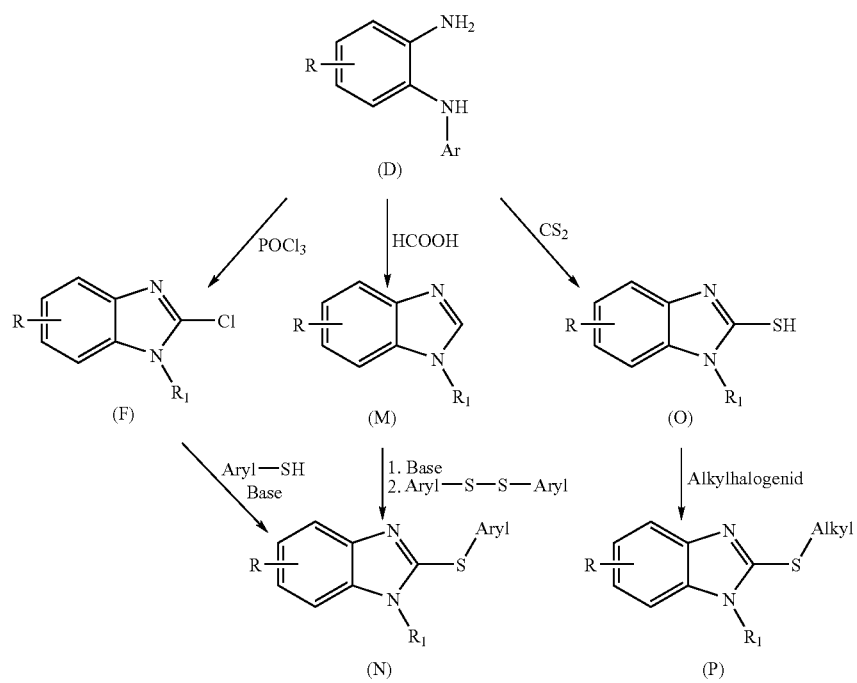

[Key:]
Alkylhalogenid = alkyl halide

From 2-chlorobenzimidazole derivatives (F), 2-arylmercaptobenzimidazoles (N) can be produced by treatment with arylthiols and bases [K. Hirai, H. Koike, T. Ishiba, S. Ueda, I. Makino et al., *Eur. J. Med. Chem. Chim. Ther.*, 1991, 143]. These 2-arylthiobenzimidazoles are also accessible by phenylenediamines of type D being cyclized with, for example, trialkylorthoformates [A. J. Freyer, C. K. Lowe-Ma, R. A. Nissan, W. S. Wilson, *Aust. J. Chem.*, 1992, 525] or with formic acid [S. Abuzar, S. Sharma, Z. *Naturforsch. B Anorg. Chem. Org. Chem.*, 1981, 108] to form 2-unsubstituted benzimidazoles (M) and these benzimidazoles then being deprotonated with strong bases and reacted with diaryl disulfides [S. Ohta et al., *J. Chem. Soc. Perkin Trans.*, 1, 2001, 429]. 2-Alkylmercaptobenzimidazoles (P) are accessible, for example, in that phenylenediamines of type D are cyclized with carbon disulfide to form 2-mercaptobenzimidazoles (O) [E. R. Lavagnino, D. C. Thompson, *J. Heterocycl. Chem.*, 1972, 149; E. L. Ellsworth, J. Domagala, J. V. N. Prasad, S. Hagen, D. Ferguson et al., *Bioorg. Med. Chem. Lett.*; 1999, 2019], which then are reacted by base-mediated S-alkylation [E. Nicolai, J. Goyard, T. Benchetrit, J.-M. Teulon, F. Caussade et al., *J. Med. Chem.*, 1993, 1176] to form the 2-alkylmercapto-benzimidazoles (P). The 2-arylmercapto- and 2-alkylmercaptobenzimidazoles (N) and (P) can be converted according to known processes, for example by reaction with m-chloroperbenzoic acid, into sulfoxides [J. C. Sih, W. B. Im, A. Robert, D. R. Graber, D. P. Blakeman, *J. Med. Chem.*, 1991, 1049; S. C. Yoon, K. Kim, *J. Org. Chem.*, 1996, 793] or sulfones [D. E. Beattie, R. Crossley, K. H. Dickinson, M. Dover, *Eur. J. Med. Chem. Chim. Ther.*, 1983, 277–285].

For one skilled in the art, it goes without saying that substituents R must be compatible with the reagents that are used during the course of the synthesis sequence and under the reaction conditions. The substituents optionally can be modified later.

Finally, it can be mentioned that in some cases, the possibility of direct N-arylation of pre-fabricated benzimidazoles exists, for example, according to M. J. Sansone, M. S. Kwiatek, U.S. Pat. No. 4,933,397 or D. M. T. Chan, K. L. Monaco, R.-P. Wang, M. P. Winters, *Tet. Lett.*, 39 (1998) 2933 or A. P. Combs, S. Saubern, M. Rafalski, P. Y. S. Lam, *Tet. Lett.*, 40 (1999) 1623.

If structural element B-A-Y (Formula I) is established in protected or unprotected form because of incompatibility with the reaction conditions during the respective benzimidazole synthesis or for other reasons of synthesis only after completion of benzimidazole synthesis, various procedures for establishing the B-A-Y structural element (Formula I) are possible depending on substituents $R^3$ that are entrained in the benzene ring of the benzimidazole skeleton, whereby, which is obvious to one skilled in the art, a compatibility of the methods used with the aryl substituents and other radicals $R^3$ must be taken into consideration.

Below, some possibilities for establishing the B-A-Y structural element are indicated:

Oxygen can be entrained from the start in free form or else in protected form, for example as alkyl ether [cf., for example: B. D. Jerchel, H. Fischer, M. Graft, *Ann. Chem.*, 575, 162 (1952)] as a substituent in a benzimidazole synthesis. By alkyl ether cleavage, for example with concentrated hydrobromic acid with the optional aid of solubilizers such as halogenated hydrocarbons or else with boron tribromide in inert solvents, such as, for example, dichloromethane, the hydroxyl group can be released. The hydroxyl group can be reacted according to known methods with optionally one terminal group B (Formula I) or alkyl- and allyl halides that contain a precursor thereof to form the ethers, whereby the reaction is carried out with the alkylating agents preferably in polar solvents, such as, for example, dimethylformamide, dimethyl sulfoxide, ethers, such as, for example, tetrahydrofuran or else lower ketones, such as acetone or methylethyl ketone, with the addition of bases, such as alkali and alkaline-earth hydrides, but preferably sodium hydride, or with the addition of alkali carbonates, such as potassium or cesium carbonate, in a temperature range of 0° C. to 120° C. In addition, a reaction can be carried out in a two-phase system under phase transfer catalysis, whereby the reactants are dissolved in a suitable inert organic solvent, such as, for example, in haloalkanes, but preferably in dichloromethane. The other phase is a solid alkali hydroxide, preferably sodium or potassium hydroxide, or else a concentrated aqueous solution of the hydroxide in question. As phase transfer catalysts, for example, quaternary ammonium salts are used. Reactions under phase transfer catalysis are preferably carried out at room temperature.

For example, a phenol derivative is dissolved in dimethylformamide and reacted to form a compound of Formula I with the addition of cesium carbonate with 6-bromohexanoic acid methyl ester at temperatures of 0° C. to 50° C. The cleavage of the ester by acidic or alkaline hydrolysis can be carried out according to methods that are known to one skilled in the art, such as, for example, with basic catalysts, such as, for example, with alkali or alkaline-earth carbonates or -hydroxides in an alcohol or the aqueous solution of an alcohol. As alcohols, aliphatic alcohols, such as, for example, methanol, ethanol, butanol, etc., are considered, but preferably methanol. Aqueous solutions of ethers, such as tetrahydrofuran, are also used. As alkali carbonates and alkali hydroxides, lithium, sodium and potassium salts can be mentioned. Preferred are the lithium and sodium salts. As alkaline-earth carbonates and hydroxides, for example, calcium carbonate, calcium hydroxide and barium carbonate are suitable. The reaction is generally carried out at −10° C. to 70° C., but preferably at 25° C. The ester cleavage can also be carried out, however, under acidic conditions, such as, for example, in aqueous hydrochloric acid, optionally with the aid of a solubilizer, such as, for example, a lower alcohol, preferably methanol.

In addition, the alkylating reagents in addition to the halogen atom can carry, as another functional group, a tetrazole in protected form, for example tritylated, from which then after alkylation, the tetrazole is released. From a nitrile that is present in the alkylating reagent or else generated later, a tetrazole can also be produced later. To this end, the alkylating product is reacted with an azide, such as, for example, tributyltin azide or sodium azide in a suitable solvent, such as, for example, in aromatic hydrocarbons by heating. Also, a nitrile can be converted by hydrolysis into a carboxylic acid group. The alkylating reagents can also contain functional groups, such as, for example, hydroxyl functions in free or protected form, which can be exchanged after conversion into leaving groups, such as, for example, tosylate, mesylate, bromide or iodide, for example, for cyanides, amines, alkyl, aryl or heteroaryl components. Also, the alkylating reagents can contain functional groups, such as, for example, halogens or optionally protected amino or mercapto groups.

The introduction of nitrogen can be carried out, for example, by nitrobenzimidazoles, which are accessible according to processes that are known in the literature [see, for example: K. Bougrin, M. Soufiaoui, *Tet. Lett.*, 36, 21, 1995, 3683–3686; J. J. V. Eynde, F. Delfosse, P. Lor, Y. V.

Haverbeke, *Tetrahedron,* 51, 20, 1995, 5813–5818; Q. Sun, B. Yan, *Bioorg. Med. Chem. Lett.,* 1998, 361–364; Sandera et al., *J. Amer. Chem. Soc.* 76, 1954, 5173], being N-arylated at the nitrogen of the benzimidazole (see above) and then the nitro group being reduced by, for example, hydrogenation in polar solvents, such as acetic acid, lower alcohols or ethyl acetates, with the addition of catalysts, such as Raney nickel or palladium on carbon, or by chemical reduction with, for example, tin in hydrochloric acid or SnCl2 (see above) to the amino group. Such established amino groups then can be mono- or bis-alkylated analogously to the hydroxy groups (see above) with alkyl halides, such as, for example, with ω-bromoalkanoic acid esters or converted into sulfonamides according to processes that are known in the literature. It is also possible, for example according to standard processes, to acylate the N-monoalkylated aminobenzimmidazoles with acid derivatives, such as, for example, acid anhydrides or acid halides, or to convert with sulfonic acid anhydrides or sulfonic acid halides to the corresponding sulfonic acid amides.

N-Aryl-2-nitrobenzenes (C), in which R stands for Cl or F, such as, for example, (5-chloro-2-nitrophenyl)phenylamine, can also be converted by reaction with primary or secondary amines into the corresponding amine-substituted N-aryl-2-nitrobenzenes [see, for example: D. Evans, T. A. Hicks, W. R. N. Williamson, W. Dawson, S. C. R. Meacock, E. A. Kitchen, *Eur. J. Med. Chem. Chim. Ther.,* 31, 7–8, 1996, 635–642]. After reduction of the nitro group and ring closure in the benzimidazole (cf. Diagrams 2–4), amine-substituted benzimidazoles of types G, H, K, L, N and P can be obtained.

Depending on the substitution provided, substituents $R^3$ are contained in the synthesis components from the start or are established if necessary at suitable sites of the synthesis sequence in question or are generated from suitable precursors that are entrained. Thus, nitro groups that are entrained can be reduced to the corresponding amines according to processes that are already described above and converted into carboxyamino groups.

Sulfonylamino groups are accessible from the amino compounds according to standard processes. Thus, for example, an amine or its hydrochloride is reacted in a suitable inert solvent, such as an aromatic hydrocarbon, for example toluene, or a haloalkane, for example, dichloromethane, with the aid of a base, such as, for example, triethylamine or pyridine, with a sulfonic acid halide at 0° C. to 120° C. Nitriles can be converted, for example, with Grignard reagents or lithium organyls into ketones or hydrolyzed into acids or amides. It is obvious to one skilled in the art that the reaction conditions that are used here must be compatible with the remaining groups that are found in the molecule.

The free acid derivatives of Formula I can be converted according to diverse processes that are known in the literature into amide derivatives or ester derivatives of Formula I.

The free acid derivatives of Formula I can also be converted with neutralization to salts with suitable amounts of the corresponding inorganic bases. For example, when the corresponding acids are dissolved in water, which contains stoichiometric amounts of the base, the solid salt is obtained after the water is evaporated or after a water-miscible solvent, for example alcohol or acetone, is added.

The amine salts are produced in the usual way. To this end, the corresponding acid is dissolved in a suitable solvent, such as, for example, ethanol, acetone, diethyl ether or benzene, and one to five equivalents of the respective amine is added to this solution. In this case, the salt usually accumulates in solid form or is isolated after the solvent is evaporated in the usual way.

The clathrates with α-, β- or γ-cyclodextrin are obtained analogously to the instructions in WO-A-87/05294. β-Cyclodextrin is preferably used.

Liposomes are produced according to the process that is described in *Pharmazie in unserer Zeit [Pharmaceutics in Our Time],* 11, 98 (1982).

The benzimidazole derivatives according to the invention are produced analogously to known processes: Processes for their production are described in, for example, EP 0 531 883 A1. If the production of the starting compounds is not described, the starting compounds are known and commercially available, or the compounds are synthesized analogously to the described processes. Below, the production of several precursors, intermediate products and products is described by way of example.

In the production of the substances according to the invention, for example, the following processes are used:

General Operating Instructions 1:

Reduction of Nitro Groups

The compound that is to be hydrogenated is dissolved in ethyl acetate, tetrahydrofuran, or ethanol or mixtures of the solvent, and it is hydrogenated to 2 to 5% (relative to the nitro compound) palladium on carbon (10%) at normal pressure. After hydrogen absorption has ended, it is suctioned off, the residue is washed with ethyl acetate or ethanol, and the filtrate is concentrated by evaporation in a vacuum. The crude product is reacted generally without further purification.

General Operating Instuctions 2:

Alkylation of PHienol Derivatives witH Alkyl Halides

A solution of 1.85 mmol of the phenol derivative in 12 ml of N,N-dimethylformamide is mixed with 1.85 mmol of cesium carbonate and 2.24 mmol of alkyl iodide. It is stirred for 12 to 96 hours, then poured onto water, taken up with ethyl acetate, the organic phase is washed four times with water, the latter is dried on sodium sulfate and concentrated by evaporation in a vacuum.

As an alternative to this aqueous working-up, the reaction mixture can be mixed with dichloromethane, separated from the precipitating salts by filtration and the filtrate concentrated by evaporation in a vacuum.

Independently of the working-up method, the residue is purified by crystallization or column chromatography on silica gel.

Genarating Operating Instructions 3:

Saponification of Carboxcylic Acid Alkyl Esters 0.77 mmol of the carboxylic acid alkyl ester is dissolved in 5 ml of methanol and 5 ml of tetrahydrofuran, and it is mixed with 5 ml of a 0.5N aqueous lithium or sodium hydroxide solution. After 2 to 12 hours of stirring, it is concentrated by evaporation in a vacuum to a very large extent, neutralized by the addition of aqueous hydrochloric acid and extracted with ethyl acetate. It is dried on sodium sulfate and concentrated by evaporation in a vacuum. The residue is purified, if necessary, by column chromatography on silica gel or by crystallization.

General Operating Instructions 4:

Conversion of Carboxylic Acid Esters to Carboxylic Acid Amides 0.36 mmol of an amine is dissolved in 3 ml of toluene and mixed drop by drop with 0.18 ml of a 2 M solution of trimethylaluminum in toluene while being cooled in an ice bath. It is mixed with a solution that consists of 0.33 mmol of carboxylic acid methyl ester in 3 ml of toluene, and it is stirred for 2 to 8 hours at 95° C. For working-up, water is added after cooling, it is extracted three times with ethyl acetate, the combined organic phases are washed with saturated sodium chloride solution, dried on sodium sulfate and concentrated by evaporation in a vacuum. The residue is purified by column chromatography on silica gel.

TABLE 1

Benzimidazole Derivatives According to the Invention

| No. | Benzimidazole derivative |
|---|---|
| 1 | 6-[[1-Phenyl-2-propylmercapto-1H-benzimidazol-6-yl]oxy]hexanoic acid methyl ester |
| 2 | 6-[[1-Phenyl-2-propanesulfinyl-1H-benzimidazol-6-yl]oxy]hexanoic acid methyl ester |
| 3 | 6-[[1-Phenyl-2-propanesulfonyl-1H-benzimidazol-6-yl]oxy]hexanoic acid methyl ester |
| 4 | 6-[[1-(4-Methylphenyl)-2-propylmercapto-1H-benzimidazol-6-yl]oxy]hexanoic acid methyl ester |
| 5 | 6-[[1-(4-Methylphenyl)-2-propanesulfinyl-1H-benzimidazol-6-yl]oxy]hexanoic acid methyl ester |
| 6 | 6-[[1-(4-Methylphenyl)-2-propanesulfonyl-1H-benzimidazol-6-yl]oxy]hexanoic acid methyl ester |
| 7 | 6-[[2-Benzylmercapto-1-(4-methylphenyl)-1H-benzimidazol-6-yl]oxy]hexanoic acid methyl ester |
| 8 | 6-[[1-(4-Methylphenyl)-2-(phenylmethanesulfinyl)-1H-benzimidazol-6-yl]oxy]hexanoic acid methyl ester |
| 9 | 6-[[1-(4-Methylphenyl)-2-(phenylmethanesulfonyl)-1H-benzimidazol-6-yl]oxy]hexanoic acid methyl ester |
| 10 | 6-[[1-(4-Methylphenyl)-2-(2-pyridinyl)mercapto-1H-benzimidazol-6-yl]oxy]hexanoic acid methyl ester |
| 11 | N-(3-Methoxypropyl)-6-[[1-(4-methylphenyl)-2-propylmercapto-1H-benzimidazol-6-yl]oxy]hexanamide |
| 12 | N-(3-Methoxypropyl)-6-[[1-(4-methylphenyl)-2-propanesulfonyl-1H-benzimidazol-6-yl]oxy]hexanamide |
| 13 | N-(3-Methoxypropyl)-6-[[2-benzylmercapto-1-(4-methylphenyl)-1H-benzimidazol-6-yl]oxy] |
| 14 | N-(3-Methoxypropyl)-6-[[1-(4-methylphenyl)-2-(-phenylmethanesulfonyl)-1H-benzimidazol-6-yl]oxy]hexanamide |
| 15 | 6-[[2-(Morpholin-4-yl)-1-phenyl-1H-benzimidazol-6-yl]oxy]hexanoic acid methyl ester |
| 16 | 6-[[2-(Piperidin-1-yl)-1-phenyl-1H-benzimidazol-6-yl]oxy]hexanoic acid methyl ester |
| 17 | 6-[[1-(4-Methylphenyl)-2-(morpholin-4-yl)-1H-benzimidazol-6-yl]oxy]hexanoic acid methyl ester |
| 18 | 6-[[1-(4-Methylphenyl)-2-(piperidin-1-yl)-1H-benzimidazol-6-yl]oxy]hexanoic acid methyl ester |
| 19 | N-(3-Methoxypropyl)-6-[[2-(morpholin-4-yl)-1-phenyl-1H-benzimidazol-6-yl]oxy]hexanamide |
| 20 | N-(3-Methoxypropyl)-6-[[2-(piperidin-1-yl)-1-phenyl-1H-benzimidazol-6-yl]oxy]hexanamide |
| 21 | 6-[[2-Methoxy-1-phenyl-1H-benzimidazol-6-yl]oxy]hexanoic acid methyl ester |
| 22 | 6-[[2-Methoxy-1-phenyl-1H-benzimidazol-6-yl]oxy]hexanoic acid |
| 23 | 6-[[2-Ethoxy-1-phenyl-1H-benzimidazol-6-yl]oxy]hexanoic acid methyl ester |
| 24 | 6-[[2-Ethoxy-1-phenyl-1H-benzimidazol-6-yl]oxy]hexanoic acid |
| 25 | 6-[[1-Phenyl-2-phenylamino-1H-benzimidazol-6-yl]oxy]hexanoic acid methyl ester |
| 26 | 6-[[1-Phenyl-2-phenylamino-1H-benzimidazol-6-yl]oxy]hexanoic acid |
| 27 | 6-[[1-(4-Methylphenyl)-2-phenylamino-1H-benzimidazol-6-yl]oxy]hexanoic acid methyl ester |
| 28 | 6-[[1-Phenyl-2-propylamino-1H-benzimidazol-6-yl]oxy]hexanoic acid methyl ester |
| 29 | 6-[[1-Phenyl-2-propylamino-1H-benzimidazol-6-yl]oxy]hexanoic acid |
| 30 | 6-[[2-(N-Methyl-N-propyl)amino-1-phenyl-1H-benzimidazol-6-yl]oxy]hexanoic acid methyl ester |
| 31 | 6-[[1-(4-Methylphenyl)-2-phenyloxy-1H-benzimidazol-6-yl]oxy]hexanoic acid |
| 32 | 6-[[1-(4-Methylphenyl)-2-phenylmercapto-1H-benzimidazol-6-yl]oxy]hexanoic acid methyl ester |
| 33 | 6-[[1-(4-Methylphenyl)-2-(phenylsulfinyl)-1H-benzimidazol-6-yl]oxy]hexanoic acid methyl ester |
| 34 | 6-[[1-(4-Methylphenyl)-2-(phenylsulfonyl)-1H-benzimidazol-6-yl]oxy]hexanoic acid methyl ester |
| 35 | 6-[[1-Phenyl-2-propylmercapto-1H-benzimidazol-6-yl]oxy]hexanoic acid |
| 36 | 6-[[1-Phenyl-2-propanesulfonyl-1H-benzimidazol-6-yl]oxy]hexanoic acid |
| 37 | 6-[(2-Benzylmercapto-1-phenyl-1H-benzimidazol-6-yl)oxy]hexanoic acid methyl ester |
| 38 | 6-[[1-Phenyl-2-(phenylmethanesulfonyl)-1H-benzimidazol-6-yl]oxy]hexanoic acid methyl ester |
| 39 | 6-[(2-Benzylmercapto-1-phenyl-1H-benzimidazol-6-yl)oxy]hexanoic acid |
| 40 | 6-[[1-Phenyl-2-(phenylmethanesulfonyl)-1H-benzimidazol-6-yl]oxy]hexanoic acid |
| 41 | 6-[[1-(4-Methylphenyl)-2-propylmercapto-1H-benzimidazol-6-yl]oxy]hexanoic acid |
| 42 | 6-[[1-(4-Methylphenyl)-2-propanesulfonyl-1H-benzimidazol-6-yl]oxy]hexanoic acid |
| 43 | 6-[[2-Benzylmercapto-1-(4-methylphenyl)-1H-benzimidazol-6-yl]oxy]hexanoic acid |
| 44 | 6-[[1-(4-Methylphenyl)-2-(phenylmethanesulfonyl)-1H-benzimidazol-6-yl]oxy]-hexanoic acid |

TABLE 2

Benzimidazole Derivatives According to the Invention

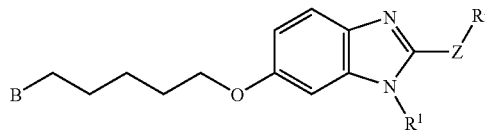

II

| Nr. | $R^1$ | $Z-R^2$ | B |
|---|---|---|---|
| 1 | Phenyl | $S-(CH_2)_2CH_3$ | $COOCH_3$ |
| 2 | Phenyl | $SO-(CH_2)_2CH_3$ | $COOCH_3$ |
| 3 | Phenyl | $SO_2-(CH_2)_2CH_3$ | $COOCH_3$ |
| 4 | p-$CH_3$-Phenyl | $S-(CH_2)_2CH_3$ | $COOCH_3$ |
| 5 | p-$CH_3$-Phenyl | $SO-(CH_2)_2CH_3$ | $COOCH_3$ |
| 6 | p-$CH_3$-Phenyl | $SO_2-(CH_2)_2CH_3$ | $COOCH_3$ |
| 7 | p-$CH_3$-Phenyl | $S-CH_2Phenyl$ | $COOCH_3$ |
| 8 | p-$CH_3$-Phenyl | $SO-CH_2Phenyl$ | $COOCH_3$ |
| 9 | p-$CH_3$-Phenyl | $SO_2-CH_2Phenyl$ | $COOCH_3$ |
| 10 | p-$CH_3$-Phenyl | S-2-Pyridiny | $COOCH_3$ |
| 11 | p-$CH_3$-Phenyl | $S-(CH_2)_2CH_3$ | $CONH(CH_2)_3OCH_3$ |
| 12 | p-$CH_3$-Phenyl | $SO_2-(CH_2)_2CH_3$ | $CONH(CH_2)_3OCH_3$ |
| 13 | p-$CH_3$-Phenyl | $S-CH_2Phenyl$ | $CONH(CH_2)_3OCH_3$ |
| 14 | p-$CH_3$-Phenyl | $SO_2-CH_2Phenyl$ | $CONH(CH_2)_3OCH_3$ |
| 15 | Phenyl | 4-Morpholinyl | $COOCH_3$ |
| 16 | Phenyl | 1-Piperidyl | $COOCH_3$ |
| 17 | p-$CH_3$-Phenyl | 4-Morpholinyl | $COOCH_3$ |
| 18 | p-$CH_3$-Phenyl | 1-Piperidyl | $COOCH_3$ |
| 19 | Phenyl | 4-Morpholinyl | $CONH(CH_2)_3OCH_3$ |

TABLE 2-continued

Benzimidazole Derivatives According to the Invention

II

| Nr. | $R^1$ | Z—$R^2$ | B |
|---|---|---|---|
| 20 | Phenyl | 1-Piperidyl | $CONH(CH_2)_3OCH_3$ |
| 21 | Phenyl | O—$CH_3$ | $COOCH_3$ |
| 22 | Phenyl | O—$CH_3$ | COOH |
| 23 | Phenyl | O—$CH_2CH_3$ | $COOCH_3$ |
| 24 | Phenyl | O—$CH_2CH_3$ | COOH |
| 25 | Phenyl | NH-Phenyl | $COOCH_3$ |
| 26 | Phenyl | NH-Phenyl | COOH |
| 27 | p-$CH_3$-Phenyl | NH-Phenyl | $COOCH_3$ |
| 28 | Phenyl | NH—$(CH_2)_2CH_3$ | $COOCH_3$ |
| 29 | Phenyl | NH—$(CH_2)_2CH_3$ | COOH |
| 30 | Phenyl | $N(CH_3)(CH_2)_2CH_3$ | $COOCH_3$ |
| 31 | p-$CH_3$-Phenyl | O-Phenyl | COOH |
| 32 | p-$CH_3$-Phenyl | S-Phenyl | $COOCH_3$ |
| 33 | p-$CH_3$-Phenyl | SO-Phenyl | $COOCH_3$ |
| 34 | p-$CH_3$-Phenyl | $SO_2$-Phenyl | $COOCH_3$ |
| 35 | Phenyl | S—$(CH_2)_2CH_3$ | COOH |
| 36 | Phenyl | $SO_2$—$(CH_2)_2CH_3$ | COOH |
| 37 | Phenyl | S—$CH_2$Phenyl | $COOCH_3$ |
| 38 | Phenyl | $SO_2$—$CH_2$Phenyl | $COOCH_3$ |
| 39 | Phenyl | S—$CH_2$Phenyl | COOH |
| 40 | Phenyl | $SO_2$—$CH_2$Phenyl | COOH |
| 41 | p-$CH_3$-Phenyl | S—$(CH_2)_2CH_3$ | COOH |
| 42 | p-$CH_3$-Phenyl | $SO_2$—$(CH_2)_2CH_3$ | COOH |
| 43 | p-$CH_3$-Phenyl | S—$CH_2$Phenyl | COOH |
| 44 | p-$CH_3$-Phenyl | $SO_2$—$CH_2$Phenyl | COOH |

EXAMPLE 1

6-[[1-Phenyl-2-propylmercapto-1H-benzimidazol-6-yl]oxy]hexanoic acid-methyl ester a) 3-Phenylamino-4-nitrophenol 14 g of 3-fluoro-4-nitrophenol and 24 ml of aniline were mixed and stirred for 3 hours at 140° C. After cooling, it was dissolved in ethyl acetate and extracted six times with 2N aqueous hydrochloric acid. The organic phase was washed with saturated sodium chloride solution, dried on sodium sulfate, concentrated by evaporation in a vacuum, and the residue was crystallized from diisopropyl ether. 20.8 g was obtained.

Flash point 170–172° C.

b) 6-(3-Phenylamino-4-nitrophenyl)oxyhexanoic acid methyl ester 13.3 g of 3-phenylamino-4-nitrophenol was reacted with 6-bromohexanoic acid methyl ester according to general operating instructions 2. 11.2 g was obtained.

$^1$H-NMR (CDCl$_3$): δ=1.38–1.52 ppm m (2H); 1.59–1.80 m (4H); 2.33 t (J=7.5 Hz, 2H); 3.67 s (3H); 3.87t (J=7.5Hz, 2H);6.32 dd (J=8.2Hz, 1H); 6.52d (J=2Hz, 1H); 7.20–7.32 m (3H); 7.40–7.48 m (2H); 8.18 d (J=8 Hz, 1H); 9.75 s (broad) (1H).

c) 6-(-3-Phenylamino-4-aminophenyl)oxyhexanoic acid methyl ester 4.5 g of 6-(3-phenylamino-4-nitrophenyl)oxyhexanoic acid methyl ester was reduced by reaction according to general operating instructions 1. 4.3 g was obtained.

$^1$H-NMR (CDCl$_3$): δ=1.42–1.52 ppm m (2H); 1.62–1.83 m (4H); 2.34 t (J=7.5 Hz, 2H); 3.68 s (3H); 3.86 t (J=7.5 Hz, 2H); 5.32 s (broad) (1H); 6.54 dd (J=8.2 Hz, 1H); 6.74d (J=8 Hz, 1H); 6.78 d (J=2 Hz, 1H); 6.80–6.90 m (3H); 7.20–7.29 m (2H).

d) 6-[[2-Mercapto-1-phenyl-1H-benzimidazol-6-yl]oxy]hexanoic acid methyl ester 0.4 g of 6-(3-phenylamino-4-aminophenyl)oxyhexanoic acid methyl ester was dissolved in 5 ml of pyridine, mixed with 75 µl of carbon disulfide, and the mixture was stirred for 12 hours at 20° C. It was mixed with saturated sodium bicarbonate solution, extracted three times with ethyl acetate, the combined organic phases were washed with saturated sodium chloride solution, dried on sodium sulfate and concentrated by evaporation in a vacuum. The residue was purified by column chromatography on silica gel. 368 mg was obtained.

Flash point 122–123° C.

e) 6-[[1-Phenyl-2-propylmercapto-1H-benzimidazol-6-yl]oxy]hexanoic acid methyl ester 100 mg of 6-[[2-mercapto-1-phenyl-1H-benzimidazol-6-yl]oxy]hexanoic acid methyl ester was dissolved in 2 ml of N,N-dimethylformamide, mixed with 40 µl of propyl iodide, 57 mg of potassium hydrogen carbonate and 10 mg of dicyclohexano-18-crown-6, and the mixture was stirred for 15 hours at 20° C. It was filtered, and the filtrate was concentrated by evaporation in a vacuum. The residue was purified by column chromatography on silica gel. 103 mg was obtained.

Flash point 45.5–47° C.

EXAMPLE 2

6-[[1-Phenyl-2-propanesulfinyl-1H-benzimidazol-6-yl]oxy]hexanoic acid methyl ester 80 mg of 6-[[1-phenyl-2-propylmercapto-1H-benzimidazol-6-yl]oxy]hexanoic acid methyl ester was dissolved in 2 ml of dichloromethane, mixed with 56 mg of m-chloroperbenzoic acid (about 60%), and the mixture was stirred for 10 minutes at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 30 mg was obtained.

$^1$H-NMR (CDCl$_3$): δ=1.06 ppm t (J=8 Hz, 3H); 1.43–1.55 m (2H); 1.62–1.85 m (6H); 2.33 t (J=7.5 Hz, 2H); 3.24–3.36 m (1H); 3.47–3.58 m (1H); 3.67 s (3H); 3.90 t (J=7.5 Hz, 2H); 6.67 d (J=2 Hz, 1H); 7.02 dd (J=8.2 Hz, 1H); 7.50–7.69 m (5H); 7.78 d (J=8 Hz, 1H).

EXAMPLE 3

6-[[1-Phenyl-2-propanesulfonyl-1H-benzimidazol-6-yl]oxy]hexanoic acid methyl ester 85 mg of 6-[[1-phenyl-2-propylmercapto-1H-benzimidazol-6-yl]oxy]hexanoic acid methyl ester was dissolved in 2 ml of dichloromethane, mixed with 59 mg of m-chloroperbenzoic acid (about 60%), and the mixture was stirred for 9 hours at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 30 mg was obtained.

MS (EI): 444 (molecular ion peak)

EXAMPLE 4

6-[[1-(4-Methylphenyl)-2-propylmercapto-1H-benzimidazol-6-yl]oxy]hexanoic acid methyl ester a) 3-(4-Methylphenyl)amino-4-nitrophenol 1.3 g of 3-fluoro-4-nitrophenol and 2.7 g of 4-methylaniline were mixed and stirred for 14 hours at 140° C. After cooling, it was dissolved in ethyl acetate and extracted three times with 4N aqueous hydrochloric acid. The organic phase was washed with saturated sodium chloride solution, dried on sodium sulfate, concentrated by evaporation in a vacuum, and the residue was crystallized from diisopropyl ether. 1.70 g was obtained.

$^1$H-NMR (CDCl$_3$): δ=2.34 ppm s (3H); 6.25 dd (J=8.2 Hz, 1H); 6.48 d (J=2 Hz, 1H); 7.12–7.20 m (4H); 8.08 d (J=8 Hz, 1H); 9.64 s (broad) (1H); 9.72 s (broad). (1H).

b) 6-[3-(4-Methylphenyl)amino-4-nitrophenyl]oxyhexanoic acid methyl ester 990 mg of 3-(4-methylphenyl)amino-4-nitrophenol was reacted with 6-bromohexanoic acid methyl ester according to general operating instructions 2. 1.5 g was obtained.

$^1$H-NMR (CDCl$_3$): δ=1.38–1.50 ppm m (2H); 1.60–1.80 m (4H); 2.33 t (J=7.5 Hz, 2H); 2.39 s (3H); 3.68 s (3H); 3.85 t (J=7.5 Hz, 2H); 6.28 dd (J=8.2 Hz, 1H); 6.45 d (J=2 Hz, 1H); 7.15 d (J=8Hz, 2H); 7.24 d (J=8 Hz, 2H); 8.18 d (J=8 Hz, 1H); 9.70 s (broad) (, 1H).

c) 6-[3-(4-Methylphenyl)amino-4-aminophenyl]oxyhexanoic acid methyl ester 1.3 g of 6-[3-(4-methylphenyl)amino-4-nitrophenyl]oxyhexanoic acid methyl ester was reduced by reaction according to general operating instructions 1. 1.19 g was obtained.

$^1$H-NMR (CDCl$_3$): δ=1.40–1.54 ppm m (2H); 1.62–1.78 m (4H); 2.30 s (3H); 2.33 t (J=7.5 Hz, 2H); 3.68 s (3H); 3.85 t (J=7.5 Hz, 2H); 5.27 s (broad) (1H); 6.50 dd (J=8.2 Hz, 1H); 6.72 d (J=2 Hz, 1H); 6.74 d (J=8 Hz, 1H); 6.80 d (J=8 Hz, 2H); 7.04 d (J=8 Hz, 2H).

d) 6-[[2-Mercapto-1-(4-methylphenyl)-1H-benzimidazol-6-yl]oxy]hexanoic acid methyl ester 3 g of 6-[3-(4-methylphenyl)-4-aminophenyl]oxyhexanoic acid methyl ester was dissolved in 15 ml of pyridine, mixed with 0.6 ml of carbon disulfide, and the mixture was stirred for 20 hours at 20° C. It was mixed with saturated sodium bicarbonate solution, extracted three times with ethyl acetate, the combined organic phases were washed with saturated sodium chloride solution, dried on sodium sulfate and concentrated by evaporation in a vacuum. The residue was crystallized from diisopropyl ether. 2.6 g was obtained.

$^1$H-NMR (CDCl$_3$): δ=1.40–1.52 ppm m (2H); 1.60–1.82 m (4H); 2.33 t (J=7.5 Hz, 2H); 2.48 s (3H); 3.66 s (3H); 3.89 t (J=7.5 Hz, 2H); 6.46 d (J=2 Hz, 1H); 6.80 dd (J=8.2 Hz, 1H); 7.16 d (J=8 Hz, 1H); 7.40 s (4H).

e) 6-[[1-(4-Methylphenyl)-2-propylmercapto-1H-benzimidazol-6-yl]oxy]hexanoic acid methyl ester 1 g of 6-[[2-mercapto-1-(4-methylphenyl)-1H-benzimidazol-6-yl]oxy]hexanoic acid methyl ester was dissolved in 15 ml of N,N-dimethylformamide, mixed with 0.3 ml of propyl iodide, 0.55 g of potassium hydrogen carbonate and 97 mg of dicyclohexano-18-crown-6, and the mixture was stirred for 48 hours at 20° C. It was filtered, and the filtrate was concentrated by evaporation in a vacuum. The residue was purified by column chromatography on silica gel. 1.06 g was obtained.

$^1$H-NMR (CDCl$_3$): δ=1.02 ppm t (J=8 Hz, 3H); 1.43–1.52 m (2H); 1.62–1.83 m (6H); 2.32 t (J=7.5 Hz, 2H); 2.48 s (3H); 3.30 t (J=8 Hz, 2H); 3.67 s (3H); 3.90 t (J=7.5 Hz, 2H); 6.56 d (J=2 Hz, 1H); 6.83 dd (J=8.2 Hz, 1H); 7.32 d (J=7.5 Hz, 2H); 7.39 d (J=7.5 Hz, 2H); 7.58 d( J=8 Hz, 1H).

EXAMPLE 5

6-[[1-(4-Methylphenyl)-2-propanesulfinyl-1H-benzimidazol-6-yl]oxy]hexanoic acid methyl ester

EXAMPLE 6

6-[[1-(4-Methylphenyl)-2-propanesulfonyl-1H-benzimidazol-6-yl]oxy]hexanoic acid methyl ester 600 mg of 6-[[1-(4-methylphenyl)-2-propylmercapto-1H-benzimidazol-6-yl]oxy]hexanoic acid methyl ester was dissolved in 10 ml of dichloromethane, mixed with 405 mg of m-chloroperbenzoic acid (about 60%), and the mixture was stirred for 15 minutes at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 525 mg of 6-[[1-(4-methylphenyl)-2-propanesulfinyl-1H-benzimidazol-6-yl]oxy]hexanoic acid methyl ester was obtained.

$^1$H-NMR (CDCl$_3$): δ=1.05 ppm t (J=8 Hz, 3H); 1.43–1.54 m (2H); 1.62–1.78 m (6H); 2.33 t (J=7.5 Hz, 2H); 2.50 s (3H); 3.25–3.35 m (IH); 3.43–3.53 m (1H); 3.67 s (3H); 3.90 t (J=7.5 Hz, 2H); 6.62 d (J=2 Hz, 1H); 7.00 dd (J=8.2 Hz, 1H); 7.40 s (4H); 7.78 d (J=8 Hz, 1H), and 239 mg of 6-[[1-(4-methylphenyl)-2-propanesulfonyl-1H-benzimidazol-6-yl]oxy]hexanoic acid methyl ester, $^1$H-NMR (CDCl$_3$): δ=1.04 ppm t (J=8 Hz, 3H); 1.42–1.54 m (2H); 1.62–1.92 m (6H); 2.34 t (J=7.5 Hz, 2H); 2.48 s (3H); 3.48 t (J=8 Hz, 2H); 3.67 s (3H); 3.88 t (J=7.5 Hz, 2H); 6.52 d (J=2 Hz, 1H); 7.00 dd (J=8.2 Hz, 1H); 7.39 s (4H); 7.76 d (J=8 Hz, 1H).

EXAMPLE 7

6-[[2-Benzylmercapto-1-(4-methylphenyl)-1H-benzimidazol-6-yl]oxy]hexanoic acid methyl ester 800 mg of 6-[[2-mercapto-1-(4-methylphenyl)-1H-benzimidazol-6-yl]oxy]hexanoic acid methyl ester was dissolved in 8 ml of N,N-dimethylformamide, mixed with 0.3 ml of benzylbromide, 438 mg of potassium hydrogen carbonate and 75 mg of dicyclohexano-18-crown-6, and the mixture was stirred for 15 hours at 20° C. It was filtered, and the filtrate was concentrated by evaporation in a vacuum. The residue was purified by column chromatography on silica gel. 976 mg was obtained.

MS (EI): 474 (molecular ion peak)

EXAMPLE 8

6-[[-(4-Methylphenyl)-2-(phenylmethanesulfinyl)-1H-benzimidazol-6-yl]oxy]hexanoic acid methyl ester

EXAMPLE 9

6-[[1-(4-Methylphenyl)-2-(phenylmethanesulfonyl)-1H-benzimidazol-6-yl]oxy]hexanoic acid methyl ester 500 mg of 6-[[2-benzylmercapto-1-(4-methylphenyl)-1H-benzimidazol-6-yl]oxy]hexanoic acid methyl ester was dissolved in 9 ml of dichloromethane, mixed with 303 mg of m-chloroperbenzoic acid (about 60%), and the mixture was stirred for 2 hours at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 232 mg of 6-[[1-(4-methylphenyl)-2-(phenylmethanesulfinyl)-1H-benzimidazol-6-yl]oxy]hexanoic acid methyl ester was obtained.

$^1$H-NMR (CDCl$_3$): δ=1.42–1.53 ppm m (2H); 1.62–1.84 m (4H); 2.32 t (J=7.5 Hz, 2H); 2.42 s (3H); 3.64 s (3H); 3.88 t (J=7.5 Hz, 2H); 4.58 d (J=12 Hz, 1H); 4.88 d (J=12 HZ, 1H); 6.50 d (J=2 Hz, 1H); 6.75–6.93 m (2H); 7.01 dd (J=8.2 Hz, 1H); 7.12 d (J=8 Hz, 2H); 7.20–7.33 m (5H); 7.82 d (J=8 Hz, 1H), and 189 mg of 6-[[1-(4-methylphenyl)-2-(phenylmethanesulfonyl)-1H-benzimidazol-6-yl]oxy]hexanoic acid methyl ester, $^1$H-NMR (CDCl$_3$): δ=1.42–1.54 ppm m (2H); 1.58–1.82 m (4H); 2.34 t (J=7.5 Hz, 2H); 2.42 s (3H); 3.67 s (3H); 3.86 t (J=7.5 Hz, 2H); 4.75 s (2H); 6.38 d (J=2 Hz, 1H); 6.86 d (J=8 Hz, 2H); 7.03 dd (J=8.2 Hz, 1H); 7.15–7.38 m (7H); 7.82 d (J=8 Hz, 1H).

EXAMPLE 10

6-[[1-(4-Methylphenyl)-2-(2-pyridinyl)mercapto-1H-benzimidazol-6-yl oxy]hexanoic acid methyl ester 200 mg of 6-[[1-(4-methylphenyl)-2-mercapto-1H-benzimidazol-6-yl]oxy]hexanoic acid methyl ester was heated to 150° C. with 80 μl of 2-chloropyridine for 14 hours. After another 200 μl of 2-chloropyridine was added, it was heated for 3 hours to 170° C. After cooling, it was purified by column chromatography on silica gel. 40 mg was obtained.

MS (EI): 461 (molecular ion peak)

EXAMPLE 11

N-(3-Methoxypropyl)-6-[[1-(4-methylphenyl)-2-propylmercapto-1H-benzimidazol-6-yl]oxy]hexanamide 100 mg of 6-[[1-(4-methylphenyl)-2-propylmercapto-1H-benzimidazol-6-yl]oxy]hexanoic acid methyl ester was reacted with 3-methoxypropylamine according to general operating instructions 4. 38 mg was obtained.

MS (EI): 483 (molecular ion peak)

EXAMPLE 12

N-(3-Methoxypropyl)-6-[[1-(4-methylphenyl)-2-propanesulfonyl-1H-benzimidazol-6-yl]oxy]hexanamide 100 mg of 6-[[1-(4-methylphenyl)-2-propanesulfonyl-1H-benzimidazol-6-yl]oxy]hexanoic acid methyl ester was reacted with 3-methoxypropylamine according to general operating instructions 4. 105 mg was obtained.

MS (EI): 515 (molecular ion peak)

EXAMPLE 13

N-(3-Methoxypropyl)-6-[[1-(4-methylphenyl)-2-benzylmercapto-1H-benzimidazol-6-yl]oxy]hexanamide 100 mg of 6-[[2-benzylmercapto-1-(4-methylphenyl)-1H-benzimidazol-6-yl]oxy]hexanoic acid methyl ester was reacted with 3-methoxypropylamine according to general operating instructions 4. 53 mg was obtained.

MS (EI): 531 (molecular ion peak)

EXAMPLE 14

N-(3-Methoxypropyl)-6-[[1-(4-methylphenyl)-2-(-phenylmethanesulfonyl)-1H-benzimidazol-6-yl]oxy]hexanamide 100 mg of 6-[[1-(4-methylphenyl)-2-(phenylmethanesulfonyl)-1H-benzimidazol-6-yl]oxy]hexanoic acid methyl ester was reacted with 3-methoxypropylamine according to general operating instructions 4. 22 mg was obtained.

MS (EI): 563 (molecular ion peak)

EXAMPLE 15

6-[[2-(Morpholin-4-yl)-1-phenyl-1H-benzimidazol-6-yl]oxy]hexanoic acid methyl ester a) 6-[[1-Phenyl-2-oxo-2,3-dihydro-1H-benzoimidazol-6-yl]oxy]hexanoic acid methyl ester 7.5 g of 6-(3-phenylamino-4-aminophenyl)oxyhexanoic acid methyl ester was mixed with 8.23 g of urea, and the mixture was heated to 140° C. for 4 hours. After cooling, it was mixed with water, extracted three times with ethyl acetate, the combined organic phases were washed with saturated sodium chloride solution, dried on sodium sulfate and concentrated by evaporation in a vacuum. The residue was crystallized from diisopropyl ether. 4.27 g was obtained. Flash point 146.5–148° C.

b) 6-[[2-Chloro-1-phenyl-1H-benzimidazol-6-yl]oxy]hexanoic acid methyl ester 3 g of 6-[[1-phenyl-2-oxo-2,3-dihydro-1H-benzoimidazol-6-yl]oxy]hexanoic acid methyl ester was mixed with 12 ml of phosphorus oxychloride, and the mixture was refluxed for 4 hours. After cooling, it was stirred into saturated sodium bicarbonate solution, extracted three times with ethyl acetate, the combined organic phases were dried on sodium sulfate and concentrated by evaporation in a vacuum. The residue was purified by column chromatography on silica gel. 1.28 g was obtained.

MS (EI): 372 (molecular ion peak)

c) 6-[[2-(Morpholin-4-yl)-1-phenyl-1H-benzimidazol-6-yl]oxy]hexanoic acid methyl ester 657 mg of 6-[[2-chloro-1-phenyl-1H-benzimidazol-6-yl]oxy]hexanoic acid methyl ester was dissolved in 13 ml of morpholine, and the mixture was stirred for 6 hours at 120° C. It was concentrated by evaporation to a very large extent in a vacuum, mixed with water, extracted with ethyl acetate, the organic phase was dried on sodium sulfate and concentrated by evaporation in a vacuum. The residue was purified by column chromatography on silica gel. 271 mg was obtained.

$^1$H-NMR (CDCl$_3$): δ=1.42–1.54 ppm m (2H); 1.55–1.80 (4H); 2.34 t (J=7.5 Hz, 2H); 3.20 t (J=7.5 Hz, 4H); 3.66 s (3H); 3.66 t (J=7.5 Hz, 4H); 3.92 t (J=7.5 Hz, 2H); 6.62 d (J=2 Hz, 1H); 6.82 dd (J=8, 2 Hz, 1H); 7.45–7.61 m (6H).

EXAMPLE 16

6-[[2-(Piperidin-1-yl)-1-phenyl-1H-benzimidazol-6-yl]oxy]hexanoic acid methyl ester 100 mg of 6-[[2-chloro-1-phenyl-1H-benzimidazol-6-yl]oxy]hexanoic acid methyl ester was dissolved in 2.5 ml of piperidine, and the mixture was stirred for 5 hours at 100° C. It was concentrated by evaporation to a very large extent in a vacuum, mixed with water, extracted with ethyl acetate, the organic phase was dried on sodium sulfate and concentrated by evaporation in a vacuum. The residue was purified by column chromatography on silica gel. 30 mg was obtained.

$^1$H-NMR (CDCl$_3$): δ=1.42–1.57 ppm m (8H); 1.63–1.80 m (4H); 2.32 t (J=7.5 Hz, 2H); 3.10–3.18 m (4H); 3.65 s (3H); 3.90 t (J=7.5 Hz, 2H); 6.62 d (J=2 Hz, 1H); 6.79 dd (J=8.2Hz, 1H); 7.40–7.58 m (6H).

EXAMPLE 17

6-[[1-(4-Methylphenyl)-2-(morpholin-4-yl)-1H-benzimidazol-6-yl]oxy]hexanoic acid methyl ester a) 6-[[1-(4-Methylphenyl)-2-oxo-2,3-dihydro-1H-benzoimidazol-6-yl]oxy]hexanoic acid methyl ester 5 g of 6-[3-(4-methylphenyl)-4-aminophenyl]oxyhexanoic acid methyl ester was mixed with 5.28 g of urea, and the mixture was heated for 5 hours to 150° C. After cooling, it was mixed with water, extracted three times with ethyl acetate, the combined organic phases were washed with saturated sodium chloride solution, dried on sodium sulfate and concentrated by evaporation in a vacuum. The residue was crystallized from diisopropyl ether. 2.54 g was obtained. Flash point 99–100° C.

b) 6-[[2-Chloro-1-(4-methylphenyl)-1H-benzimidazol-6-yl]oxy]hexanoic acid methyl ester 2.5 g of 6-[[1-(4-methylphenyl)-2-oxo-2,3-dihydro-1H-benzoimidazol-6-yl]oxy]hexanoic acid methyl ester was mixed with 10 ml of phosphorus oxychloride, and the mixture was refluxed for 2 hours. After cooling, it was stirred into saturated sodium bicarbonate solution, extracted three times with ethyl acetate, the combined organic phases were dried on sodium sulfate and concentrated by evaporation in a vacuum. The residue was purified by column chromatography on silica gel. 1.28 g was obtained.

$^1$H-NMR (CDCl$_3$): δ=1.42–1.54 ppm m (2H); 1.60–1.84 m (4H); 2.34 t (J=7.5 Hz, 2H); 2.50 s (3H); 3.66 s (3H); 3.88 t (J=7.5 Hz, 2H); 6.58 d (J=2 Hz, 1H); 6.92 d (J=8 Hz, 1H); 7.30 d (J=7.5 Hz, 2H); 7.40 d (J=7.5 Hz, 2H); 7.60 d (J=8 Hz, 1H).

c) 6-[[1-(4-Methylphenyl)-2-(morpholin-4-yl)-1H-benzimidazol-6-yl]oxy]hexanoic acid methyl ester 240 mg of 6-[[2-chloro-1-(4-methylphenyl)-1H-benzimidazol-6-yl]oxy]hexanoic acid methyl ester was mixed with 0.2 ml of N,N-dimethylformamide and 0.7 ml of morpholine, and the mixture was stirred for 7.5 hours at 110° C. Another 0.7 ml of morpholine was added and heated for another 4 hours at 110° C. It was mixed with water, extracted with ethyl acetate, the organic phase was dried on sodium sulfate and concentrated by evaporation in a vacuum. The residue was purified by column chromatography on silica gel. 7 mg was obtained.

$^1$H-NMR (CDCl$_3$): δ=1.42–1.53 ppm m (2H); 1.60–1.82 m (4H); 2.34 t (J=7.5 Hz, 2H); 2.50 s (3H); 3.20 t (J=7.5 Hz, 4H); 3.68 s (3H); 3.68 t (J=7.5 Hz, 4H); 3.90 t (J=7.5 Hz, 2H); 6.60 d (J=2 Hz, 1H); 6.80 dd (J=8.2 Hz, 1H); 7.38 s (4H); 7.48 d (J=8 Hz, 1H).

EXAMPLE 18

6-[[1-(4-Methylphenyl)-2-(piperidin-1-yl)-1H-benzimidazol-6-yl]oxy]hexanoic acid methyl ester 240 mg of 6-[[2-chloro-1-(4-methylphenyl)-1H-benzimidazol-6-yl]oxy]hexanoic acid methyl ester was mixed with 0.2 ml of N,N-dimethylformamide and 0.75 ml of piperidine, and the mixture was stirred for 7.5 hours at 110° C. Another 0.75 ml of piperidine was added, and it was heated for another 4 hours at 110° C. It was mixed with water, extracted with ethyl acetate, the organic phase was dried on sodium sulfate and concentrated by evaporation in a vacuum. The residue was purified by column chromatography on silica gel. 16 mg was obtained.

$^1$H-NMR (CDCl$_3$): δ=1.40–1.58 ppm m (8H); 1.62–1.82 m (4H); 2.32 t (J=7.5 Hz, 2H); 2.48 s (3H); 3.14–3.22 m (4H); 3.68 s (3H); 3.88 t (J=7.5 Hz, 2H); 6.58 d (J=7.5 Hz, 1H); 6.78 dd (J=8.2 Hz, 1H); 7.36 s (4H); 7.50 d (J=8 Hz, 1H).

EXAMPLE 19

N-(3-Methoxypropyl)-6-[[2-(morpholin-4-yl)-1-phenyl-1H-benzimidazol-6-yl]oxy]hexanamide 135 mg of 6-[[2-(morpholin4-yl)-1-phenyl-1H-benzimidazol-6-yl]oxy]hexanoic acid methyl ester was reacted with 3-methoxypropylamine according to general operating instructions 4. 94 mg was obtained.

MS (EI): 480 (molecular ion peak)

EXAMPLE 20

N-(3-Methoxypropyl)-6-[[2-(piperidin-1-yl)-1-phenyl-1H-benzimidazol-6-yl]oxy]hexanamide 100 mg of 6-[[2-(piperidin-1-yl)-1-phenyl-1H-benzimidazol-6-yl]oxy]hexanoic acid methyl ester was reacted with 3-methoxypropylamine according to general operating instructions 4. 47 mg was obtained.

$^1$H-NMR (CDCl$_3$): δ=1.40–1.55 ppm m (8H); 1.60–1.80 m (4H); 2.18 t (J=7.5 Hz, 2H); 3.14–3.24 m (4H); 3.36 s (3H); 3.36–3.42 m (2H); 3.45 t (J=7.5 Hz, 2H); 3.90 t (J=7.5 Hz, 2H); 6.00 s (broad) (1H); 6.62 d (J=2 Hz, 1H); 6.80 d (J=8.2 Hz, 1H); 7.40–7.62 m (6H).

EXAMPLE 21

6-[[2-Methoxy-1-phenyl-1H-benzimidazol-6-yl]oxy]hexanoic acid methyl ester 200 mg of 6-(3-phenylamino-4-aminophenyl)oxyhexanoic acid methyl ester was mixed with 0.12 ml of tetramethylorthocarbonate and 40 μl of acetic acid, and the mixture was heated for 4 hours to 80° C. After cooling, it was mixed with 1N sodium hydroxide solution, extracted three times with ethyl acetate, the combined organic phases were washed with saturated sodium chloride solution, dried on sodium sulfate and concentrated by evaporation in a vacuum. The residue was purified by column chromatography on silica gel. 104 mg was obtained.

Flash point 104–106° C.

EXAMPLE 22

6-[[2-Methoxy-1-phenyl-1H-benzimidazol-6-yl]oxy]hexanoic acid 56 mg of 6-[[2-methoxy-1-phenyl-1H-benzimidazol-6-yl]oxy]hexanoic acid methyl ester was reacted according to general operating instructions 3.33 mg was obtained.

Flash point 134–136° C.

EXAMPLE 23

6-[[2-Ethoxy-1-phenyl-1H-benzimidazol-6-yl]oxy]hexanoic acid methyl ester 200 mg of 6-(3-phenylamino-4-aminophenyl)oxyhexanoic acid methyl ester was mixed with 0.19 ml of tetraethylorthocarbonate and 40 μl of acetic acid, and the mixture was heated for 4 hours to 80° C. After cooling, it was mixed with 1N sodium hydroxide solution, extracted three times with ethyl acetate, the combined organic phases were washed with saturated sodium chloride solution, dried on sodium sulfate and concentrated by evaporation in a vacuum. The residue was purified by column chromatography on silica gel. 124 mg was obtained.

$^1$H-NMR (CDCl$_3$): δ=1.45 ppm t (J=8 Hz, 3H); 1.45–1.55 m (2H); 1.63–1.85 m (4H); 2.35 t (J=7.5 Hz, 2H); 3.67 s (3H); 3.95 t (J=7.5 Hz, 2H); 4.60 t (J=8 Hz, 2H); 6.72 d (J=2 Hz, 1H); 6.83 dd (J=8.2 Hz, 1H); 7.40–7.60 m (6H).

EXAMPLE 24

6-[[2-Ethoxy-1-phenyl-1H-benzimidazol-6-yl]oxy]hexanoic acid 50 mg of 6-[[2-ethoxy-1-phenyl-1H-benzimidazol-6-yl]oxy]hexanoic acid methyl ester was reacted according to general operating instructions 3. 44 mg was obtained.

Flash point 127–130° C.

EXAMPLE 25

6-[[1-Phenyl-2-phenylamino-1H-benzimidazol-6-yl]oxy]hexanoic acid methyl ester 200 mg of 6-(3-phenylamino-4-aminophenyl)oxyhexanoic acid methyl ester was dissolved in 1 ml of 1,2-dichloroethane, the solution was mixed with 85 μl of phenylisocyanide dichloride, and the mixture was heated for 6 hours to 65° C. After cooling, it was mixed with water, extracted three times with ethyl acetate, the combined organic phases were washed with saturated sodium chloride solution, dried on sodium sulfate and concentrated by evaporation in a vacuum. The residue was purified by column chromatography on silica gel. 55 mg was obtained.

MS (EI): 429 (molecular ion peak)

EXAMPLE 26

6-[[1-Phenyl-2-phenylamino-1H-benzimidazol-6-yl]oxy]hexanoic acid 50 mg of 6-[[1-phenyl-2-phenylamino-1H-benzimidazol-6-yl]oxy]hexanoic acid methyl ester was reacted according to general operating instructions 3. 33 mg was obtained.

Flash point 148–149.5° C.

EXAMPLE 27

6-[[1-(4-Methylphenyl)-2-phenylamino-1H-benzimidazol-6-yl]oxy]hexanoic acid methyl ester 250 mg of 6-[3-(4-methylphenyl)-4-aminophenyl]oxyhexanoic acid methyl ester was dissolved in 1 ml of 1,2-dichloroethane, the solution was mixed with 0.1 ml of phenylisocyanide dichloride, and the mixture was heated for 8 hours to 65° C. After cooling, it was mixed with water, extracted three times with ethyl acetate, the combined organic phases were washed with saturated sodium chloride solution, dried on sodium sulfate and concentrated by evaporation in a vacuum. The residue was crystallized from a mixture that consists of ethyl acetate and diethyl ether. 147 mg was obtained.

Flash point 142–143.5° C.

EXAMPLE 28

6-[[1-Phenyl-2-propylamino-1H-benzimidazol-6-yl]oxy]hexanoic acid methyl ester 200 mg of 6-(3-phenylamino-4-aminophenyl)oxyhexanoic acid methyl ester was dissolved in 2 ml of methanol, the solution was mixed with 90 µl of propylisothiocyanate, and the mixture was heated for 3 hours to 50° C. After cooling, it was mixed with saturated ammonium chloride solution, diluted with water, extracted three times with ethyl acetate, the combined organic phases were washed with saturated sodium chloride solution, dried on sodium sulfate and concentrated by evaporation in a vacuum. The residue was purified by column chromatography on silica gel. 140 mg of a thiourea derivative, which was dissolved in 1.5 ml of methanol, was obtained. 0.16 ml of iodomethane was added to this solution, and it was refluxed for 4 hours. After cooling, it was mixed with IN aqueous hydrochloric acid, extracted three times with ethyl acetate, the combined organic phases were washed with saturated sodium chloride solution, dried on sodium sulfate and concentrated by evaporation in a vacuum. The residue was purified by column chromatography on silica gel. 72 mg was obtained.

MS (EI): 395 (molecular ion peak)

EXAMPLE 29

6-[[1-Phenyl-2-propylamino-1H-benzimidazol-6-yl]oxy]hexanoic acid 30 mg of 6-[[1-phenyl-2-propylamino-1H-benzimidazol-6-yl]oxy]hexanoic acid methyl ester was reacted according to general operating instructions 3. 17 mg was obtained.
Flash point 123–125° C.

EXAMPLE 30

6-[[2-(N-Methyl-N-propyl)amino-1-phenyl-1H-benzimidazol-6-yl oxy]hexanoic acid methyl ester 20 mg of 6-[[1-phenyl-2-propylamino-1H-benzimidazol-6-yl]oxy]hexanoic acid methyl ester was dissolved in 1 ml of tetrahydrofuran. 10 mg of sodium hydride (80% in mineral oil) was added, it was stirred for 30 minutes at 20° C., then 50 µl of iodomethane was added at 0° C., and it was stirred for 1 hour at 0° C. It was mixed with saturated ammonium chloride solution, diluted with water, extracted three times with ethyl acetate, the combined organic phases were washed with saturated sodium chloride solution, dried on sodium sulfate and concentrated by evaporation in a vacuum. The residue was purified by column chromatography on silica gel. 6 mg was obtained.

$^1$H-NMR (CDCl$_3$): δ=0.70 ppm t (J=7.5 Hz, 3H); 1.38–1.53 m (4H); 1.63–1.83 m (4H); 2.31 t (J=7.5 Hz, 2H), 2.82 s (3H); 3.02 t (J=7.5 Hz, 2H); 3.67 s (3H); 3.88 t (J=7.5 Hz, 2H); 6.53 d (J=2 Hz, 1H); 6.77 dd (J=8.2 Hz, 1H); 7.40–7.60 m (6H).

EXAMPLE 31

6-[[1-(4-Methylphenyl)-2-phenyloxy-1H-benzimidazol-6-yl]oxy]hexanoic acid 150 mg of 6-[[2-chloro-1-(4-methylphenyl)-1H-benzimidazol-6-yl]oxy]hexanoic acid methyl ester was dissolved in 2 ml of dimethylformamide, mixed with 54 mg of potassium carbonate and 37 mg of phenol, and the mixture was stirred for 7 days at 150° C. After cooling, it was mixed with saturated ammonium chloride solution, diluted with water, extracted three times with ethyl acetate, the combined organic phases were washed with saturated sodium chloride solution, dried on sodium sulfate and concentrated by evaporation in a vacuum. The residue was purified by column chromatography on silica gel. 78 mg was obtained.

MS (EI): 430 (molecular ion peak)

EXAMPLE 32

6-[[1-(4-Methylphenyl)-2-phenylmercapto-1H-benzimidazol-6-yl]oxy]hexanoic acid methyl ester 150 mg of 6-[[2-chloro-1-(4-methylphenyl)-1H-benzimidazol-6-yl]oxy]hexanoic acid methyl ester was dissolved in 2 ml of dimethylformamide, mixed with 54 mg of potassium carbonate and 40 µl of thiophenol, and the mixture was stirred for 5 hours at 140° C. After cooling, it was mixed with saturated ammonium chloride solution, diluted with water, extracted three times with ethyl acetate, the combined organic phases were washed with saturated sodium chloride solution, dried on sodium sulfate and concentrated by evaporation in a vacuum. 158 mg was obtained.

$^1$H-NMR (CDCl$_3$): δ=1.40–1.52 ppm m (2H); 1.60–1.82 m (6H); 2.32 t (J=7.5 Hz, 2H); 2.45 s (3H); 3.65 s (3H); 3.91 t (J=7.5 Hz, 2H); 6.52 d (J=2 Hz, 1H); 6.90 dd (J=8.2 Hz, 1H); 7.10–7.44 m (9H); 7.68 d (J=8 Hz, 1H).

EXAMPLE 33

6-[[1-(4-Methylphenyl)-2-(phenylsulfinyl)-1H-benzimidazol-6-yl]oxy]hexanoic acid methyl ester

EXAMPLE 34

6-[[1-(4-Methylphenyl)-2-(phenylsulfonyl)-1H-benzimidazol-6-yl]oxy]hexanoic acid methyl ester 180 mg of 6-[[1–4-methylphenyl)-2-phenylmercapto-1H-benzimidazol-6-yl]oxy]hexanoic acid methyl ester was dissolved in 4 ml of dichloromethane, mixed with 112 mg of m-chloroperbenzoic acid (about 55%), and the mixture was stirred for 5 hours at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 56 mg of 6-[[1-(4-methylphenyl)-2-(phenylsulfinyl)-1H-benzimidazol-6-yl]oxy]hexanoic acid methyl ester was obtained.

$^1$H-NMR (CDCl$_3$): δ=1.40–1.50 ppm m (2H); 1.60–1.80 m (6H); 2.30 t (J=7.5 Hz, 2H); 2.48 s (3 H); 3.64 s (3H); 3.85 t (J=7.5 Hz, 2H); 6.48 d (J=2 Hz, 1H); 6.9 Hz, 1H); 7.02–7.12 m (2H); 7.20–7.45 m (7H); 7.78 d (J=8 Hz, 1H)

and 39 mg of 6-[[1-(4-methylphenyl)-2-(phenylsulfonyl)-1H-benzimidazol-6-yl]oxy]-hexanoic acid methyl ester, $^1$H-NMR (CDCl$_3$): δ=1.38–1.52 ppm m (2H); 1.60–1.80 m (6H); 2.30 t (J=7.5 Hz, 2H); 2.50 s (3H); 3.64 s (3H); 3.83 t (J=7.5 Hz, 2H); 6.38 d (J=2 Hz, 1H); 6.98 dd (J=8.2 Hz, 1H); 7.10 d (J=8 Hz, 2H); 7.27 d (J=8Hz, 2H); 7.43 dd (J=8.8 Hz, 2H); 7.58 m (1H); 7.72 d (J=8.8 Hz, 2H); 7.78 d (J=8 Hz, 1H).

EXAMPLE 35

6-[[1-Phenyl-2-propylmercapto-1H-benzimidazol-6-yl]oxy]hexanoic acid 109 mg of 6-[[1-phenyl-2-propylmercapto-1H-benzimidazol-6-yl]oxy]hexanoic acid methyl ester was reacted according to general operating instructions 3 with lithium hydroxide. 104 mg was obtained.

MS (EI): 398 (molecular ion peak)

EXAMPLE 36

6-[[1-Phenyl-2-propanesulfonyl-1H-benzimidzol-6-yl]oxy]hexanoic acid 228 mg of 6-[[1-phenyl-2-propanesulfonyl-1H-benzimidazol-6-yl]oxy]hexanoic acid methyl ester was reacted with lithium hydroxide according to general operating instructions 3. 152 mg was obtained.

$^1$H-NMR (CDCl$_3$): δ=1.03 ppm t (J=8 Hz, 3H); 1.45–1.60 m (2H); 1.62–1.95 m (6H); 2.36 t (J=7.5 Hz, 2H); 3.45–3.56 m (2H); 3.90 t (J=7.5 Hz, 2H); 6.51 d (J=2 Hz, 1H); 7.02 dd (J=8.2 Hz, 1H); 7.48–7.66 m (5H); 7.77 d (J=8 Hz, 1H).

EXAMPLE 37

6-[(2-Benzylmercapto-1-phenyl-1H-benzimidazol-6-yl)oxy]hexanoic acid methyl ester 490 mg of 6-[(2-mercapto-1-phenyl-1H-benzimidazol-6-yl)oxy]hexanoic acid methyl ester was dissolved in 7 ml of N,N-dimethylformamide, mixed with 0.19 ml of benzyl bromide, 278 mg of potassium bicarbonate and 49 mg of dicyclohexano-18-crown-6, and the mixture was stirred for 15 hours at 20° C. It was filtered, and the filtrate was concentrated by evaporation in a vacuum. The residue was purified by column chromatography on silica gel. 548 mg was obtained.

$^1$H-NMR (CDCl$_3$): δ=1.43–1.55 ppm m (2H); 1.62–1.83 m (6H); 2.32 t (J=7.5 Hz, 2H); 3.68 s (3H); 3.90 t (J=7.5 Hz, 2H); 4.58 s (2H); 6.69 d (J=2 Hz, 1H); 6.90 dd (J=8.2 Hz, 1H); 7.20–7.59 m (10H); 7.69 d (J=8 Hz, 1H).

EXAMPLE 38

6-[[1-Phenyl-2-(phenylmethanesulfonyl)-1H-benzimidazol-6-yl]oxy]hexanoic acid methyl ester 300 mg of 6-[(2-benzylmercapto-1-phenyl-1H-benzimidazol-6-yl)oxy]hexanoic acid methyl ester was dissolved in 6 ml of dichloromethane, mixed with 468 mg of m-chloroperbenzoic acid (about 60%), and the mixture was stirred for 48 hours at 20° C. It was mixed with sodium disulfite solution, extracted twice with dichloromethane, the combined organic phases were washed with saturated sodium bicarbonate solution, water and saturated sodium chloride solution, dried on sodium sulfate and concentrated by evaporation in a vacuum. The residue was purified by column chromatography on silica gel. 179 mg was obtained.

$^1$H-NMR (CDCl$_3$): δ=1.42–1.55 ppm m (2H); 1.58–1.84 m (4H); 2.33 t (J=7.5 Hz, 2H); 3.66 s (3H); 3.85 t (J=7.5 Hz, 2H); 4.75 s (2H); 6.38 d (J=2 Hz, 1H); 6.96 dd (J=8.2 Hz, 2H); 7.04 dd (J=8.2 Hz, 1H); 7.20–7.50 m (8H); 7.82 d (J=8 Hz, 1H).

EXAMPLE 39

6-[(2-Benzylmercapto-1-phenyl-1H-benzimidazol-6-yl)oxy]hexanoic acid 235 mg of 6-[(2-benzylmercapto-1-phenyl-1H-benzimidazol-6-yl)oxy]hexanoic acid methyl ester was reacted with lithium hydroxide according to general operating instructions 3. 179 mg was obtained.

MS (EI): 446 (molecular ion peak)

EXAMPLE 40

6-[[1-Phenyl-2-(phenylmethanesulfonyl)-1H-benzimidazol-6-yl]oxy]hexanoic acid 175 mg of 6-[[1-phenyl-2-(phenylmethanesulfonyl)-1H-benzimidazol-6-yl]oxy]hexanoic acid methyl ester was reacted with lithium hydroxide according to general operating instructions 3. 143 mg was obtained.

$^1$H-NMR (CDCl$_3$): δ=1.42–1.88 m (6H); 2.38 t (J=7.5 Hz, 2H); 3.85 t (J=7.5 Hz, 2H); 4.75 s (2H); 6.38 d (J=2 Hz, 1H); 6.97 dd (J=8.2 Hz, 2H); 7.06 dd (J=8.2 Hz, 1H); 7.18–7.50 m (8H); 7.83 d (J=8 Hz, 1H).

EXAMPLE 41

6-[[1-(4-Methylphenyl)-2-propylmercapto-1H-benzimidazol-6-yl]oxy]hexanoic acid 128 mg of 6-[[1-(4-methylphenyl)-2-propylmercapto-1H-benzimidazol-6-yl]oxy]hexanoic acid methyl ester was reacted with lithium hydroxide according to general operating instructions 3. 98 mg was obtained.

MS (EI): 412 (molecular ion peak)

EXAMPLE 42

6-[[1-(4-Methylphenyl)-2-propanesulfonyl-1H-benzimidazol-6-yl]oxy]hexanoic acid 147 mg of 6-[[1-(4-methylphenyl)-2-propanesulfonyl-1H-benzimidazol-6-yl]oxy]hexanoic acid methyl ester was reacted with lithium hydroxide according to general operating instructions 3. 71 mg was obtained.

MS (EI): 444 (molecular ion peak)

EXAMPLE 43

6-[[2-Benzylmercapto-1-(4-methylphenyl)-1H-benzimidazol-6-yl]oxy]hexanoic acid 130 mg of 6-[[2-benzylmercapto-1-(4-methylphenyl)-1H-benzimdiazol-6-yl]oxy]hexanoic acid methyl ester was reacted with lithium hydroxide according to general operating instructions 3. 120 mg was obtained.

MS (EI): 460 (molecular ion peak)

EXAMPLE 44

6-[[1-(4-Methylphenyl-2-(phenylmethanesulfonyl)-1H-benzimdiazol-6-yl]-oxy]hexanoic acid 293 mg of 6-[[1-(4-methylphenyl)-2-(phenylmethanesulfonyl)-1H-benzimidazol-6-yl]oxy]hexanoic acid methyl ester was reacted with lithium hydroxide according to general operating instructions 3. 14 mg was obtained.

MS (EI): 492 (molecular ion peak)

EXAMPLE 45

Inhibition of Microglia Activation

For in vitro production of Aβ-activated microglia, primary rat microglia with synthetic Aβ-peptide are incubated:

For simulation of Aβ deposits, synthetic Aβ peptide is dried on 96-hole tissue culture plates. A peptide stock solution is diluted by 2 mg/ml of $H_2O$ 1:50 in $H_2O$. To coat the 96-hole plates, 30 μl of this dilute peptide solution/hole is used, and it is dried overnight at room temperature.

Primary rat microglia are harvested by mixed glia cultures, which were obtained from P3 rat brains. In the production of mixed glia cultures, the brains are taken from 3-day-old rats, and meninges are removed. The isolation of cells is achieved by trypsinization (0.25% trypsin solution, 15 minutes, 37° C.)). After undigested tissue fragments are separated with the aid of a 40 μm nylon mesh, the isolated cells are centrifuged off (800 rpm/10 minutes). The cell pellet is resuspended in the culture medium and moved into 100 ml tissue culture flasks (1 brain/tissue culture flask). The cultivation of the cells is carried out over a period of 5 to 7 days in Dulbeccos Modified Eagle Medium (DMEM, with glutamine), supplemented with penicillin (50 U/ml), streptomycin (40 μg/ml) and 10% (v/v) fetal calf serum (FCS) at 37° C. and 5% $CO_2$. During this incubation, an adhesive cellular film is formed, which mainly consists of astrocytes. Microglia proliferate as non-adhesive or weakly adhesive cells on the latter and are harvested via shaking incubation (420 rpm, 1 hour).

To activate the microglia by Aβ-peptide, $2.5 \times 10^4$ microglia/hole are grown on the Aβ-coated tissue culture plates and incubated over a period of 7 days in DMEM (with glutamine), supplemented with penicillin (50 U/ml), streptomycin (40 μg/ml) and 10% (v/v) fetal calf serum (FCS) at 37° C. and 5% $CO_2$. On day 5, a compound according to the invention is added at various concentrations (0.1, 0.3, 1.3 and 10 μM).

To quantify the microglia reactivity, the metabolic activity is measured on cultivation day 7 via the reduction of MTS (3-(4,5-dimethylthiazol-2-yl)-5-(3-carboxymethoxyphenyl)-2-(sulfophenyl)-2H-tetrazolium), Owen's reagent, Baltrop, J. A. et al. *Bioorg. & Med. Chem. Lett.*, 1, 6111 (1991)). The percentage of inhibition relates to a control that is treated only with DMSO. The compounds according to the invention inhibit the microglia activation. The compound of Example 9 (6-[[1-(4-methylphenyl)-2-(phenylmethanesulfonyl)-1H-benzimidazol-6-yl]oxy]hexanoic acid methyl ester shows an inhibition of $IC_{50}$=0.46 μM and the compound of Example 15 6-[[2-(morpholin-4-yl)-1-phenyl-1H-benzimidazol-6-yl]oxy]hexanoic acid methyl ester shows an inhibition of $IC_{50}$=0.87 μM.

The invention claimed is:

1. A benzimidazole derivative of general formula I:

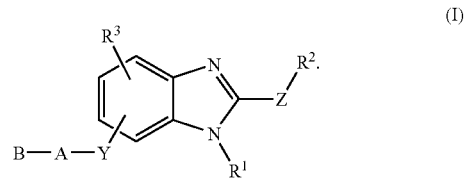

in which
$R^1$ stands for an aryl group,
whereby the aryl group is optionally substituted with up to three radicals, independently of one another selected from the group consisting of F, Cl, Br, $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$, X—OH, X—$OR^4$, X—$OCOR^4$, X—$OCONHR^4$, X—$COR^4$, X—$C(NOH)R^4$, X—CN, X—COOH, X—$COOR^4$, X—$CONH_2$, X—$CONR^4R^{4'}$, X—$CONHR^4$, X—CONHOH, X—$SR^4$, X—$SOR^4$, X—$SO_2R^4$, $SO_2NH_2$, $SO_2NHR^4$, $SO_2NR^4R^{4'}$, $NO_2$, X—$NH_2$, X—$NHR^4$, X—$NR^4R^{4'}$, X—$NHSO_2R^4$, X—$NR^4SO_2R^{4'}$, X—$NHCOR^4$, X—$NHCOOR^4$, X—$NHCONHR^4$ and $R^4$,
whereby two substituents at $R^1$ in each case can be linked to one another in such a way that they jointly form a methanediylbisoxy, ethane-1,2-diylbisoxy, propane-1,3-diyl or butane-1,4-diyl group if the substituents at $R^1$ are in ortho-position to one another,
X is a bond, $CH_2$, $(CH_2)_2$ or $CH(CH_3)$,
Z stands for a grouping that is selected from the group consisting of NH, $NR^{2'}$ and O,
$R^2$ and $R^{2'}$ idependently of one another stand for a radical that is selected from the group consisting of $C_{1-4}$-perfluoroalkyl, $C_{1-6}$-alkyl, ($C_{0-3}$-alkanediyl-$C_{3-7}$-cycloalkyl), ($C_{0-3}$-alkanediylaryl) and ($C_{0-3}$-alkanediyl-heteroaryl),
whereby the heteroaryl group is five- or six-membered and contains one or two heteroatoms selected from the group consisting of N, S and O, and
whereby the aryl and/or heteroaryl group in each case is optionally substituted with up to two radicals selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$and/or can carry an anellated methanediylbisoxy group and/or ethane-1,2-diylbisoxy group, and
whereby a ring member in the cycloalkyl ring can also be ring-N or ring-O if the cycloalkyl ring is five-membered, or one or two ring members in the cycloalkyl ring can be respectively ring-N and/or ring-O atoms if the cycloalkyl ring is six- or seven-membered, and
whereby the ring-N atoms are optionally substituted with $C_{1-3}$-alkyl or $C_{1-3}$-alkanoyl,
or if Z is $NR^{2'}$, $R^2$ and $R^{2'}$ together with Z optionally can form a five- to seven-membered heterocyclic ring, whereby the heterocyclic ring can be saturated and can contain another N, O or S atom, and can be substituted with a radical that is selected from the group consisting of $C_{1-4}$-alkyl, ($C_{0-3}$-alkanediyl-$C_{1-3}$ alkoxy), $C_{1-4}$-alkanoyl, $C_{1-4}$-alkoxycarbonyl, aminocarbonyl and phenyl, $R^3$ stands for one or two substituents, that independently of one another, are selected from the group consisting of hydrogen, F, Cl, Br, OH, $OR^4$, $OCOR^4$, $OCONHR^4$, $COR^4$, CN, COOH, $COOR^4$, $CONH_2$, $CONHR^4$, $CONR^4R^{4'}$, CONHOH, $CONHOR^4$, $SR^4$, $SOR^4$, $SO_2R^4$, $SO_2NH_2$, $SO_2NHR^4$, $SO_2NR^4R^{4'}$, $NO_2$, $NH_2$, $NHR^4$, $NR^4R^{4'}$, $NHSO_2R^4$, $NR^4SO_2R^{4'}$, $NHSO_2R^6$, $NR^4SO_2R^6$, $NHCOR^4$, $NHCOOR^4$, $NHCONHR^4$ and $R^4$, A stands for a group that is selected from the group consisting of $C_{1-10}$-alkanediyl, $C_{2-10}$-alkenediyl, $C_{2-10}$-alkinediyl and ($C_{0-3}$-alkanediyl-$C_{3-7}$-cycloalkanediyl-$C_{0-3}$-alkanediyl), whereby a ring member in the cycloalkyl ring can be ring-N or ring-O if the cycloalkyl ring is five-membered, or one or two ring members in the cycloalkyl ring in each case can be ring-N and/or ring-O atoms if the cycloalkyl ring is six- or seven-membered, whereby the ring-N atoms can be substituted with at least one radical that is selected from the group consisting of $C_{1-3}$-alkyl and $C_{1-3}$-alkanoyl radicals, whereby in the aliphatic chains of the $C_{1-10}$-alkanediyl, $C_{2-10}$-alkenediyl, $C_{2-10}$-alkinediyl and ($C_{0-3}$-alkanediyl-$C_{3-7}$-cycloalkanediyl-$C_{0-3}$-alkanediyl) groups, a C atom can also be exchanged for O, NH, N—$C_{1-3}$-alkyl or N—$C_{1-3}$-alkanoyl and whereby at least one of the alkyl and cycloalkyl groups can be substituted with a radical that is selected from the group consisting of =O, OH, O—$C_{1-3}$-alkyl, $NH_2$, NH—$C_{1-3}$-alkyl, NH—$C_{1-3}$-alkanoyl, N($C_{1-3}$-alkyl)$_2$ and N($C_{1-3}$-alkyl)($C_{1-3}$-alkanoyl), B stands for a radical that is selected from the group consisting of COOH, $COOR^5$, $CONH_2$, $CONHNH_2$, $CONHR^5$, $CONR^5R^{5'}$, CONHOH, $CONHOR^5$ and tetrazolyl, whereby B is bonded to a C atom of group A, Y stands for a group that is selected from the group consisting of O, $NR^4$, $NCOR^4$, $NSO_2R^4$ and $NSO_2R^6$, $R^4$ and $R^{4'}$ indepedently of one another stand for a radical that is selected from the group consisting of $CF_3$, $C_2F_5$, $C_{1-4}$-alkyl, $C_{2-4}$-alkenyl, $C_{2-3}$-alkinyl and ($C_{0-3}$-alkanediyl-$C_{3-7}$-cycloalkyl), whereby a ring member in the cycloalkyl ring can be ring-N or ring-O if the cycloalkyl ring is five-membered, or one or two ring members in the cycloalkyl ring can be ring-N and/or ring-O atoms in each case if the cycloalkyl ring is six- or seven-membered, whereby the ring-N atoms can be substituted with $C_{1-3}$-alkyl or $C_{1-3}$-alkanoyl, $R^5$ and $R^{5'}$ independently of one another stand for a radical that is selected from the group consisting of $C_{1-6}$-alkyl, $C_{2-6}$-alkenyl, $C_{2-6}$-alkinyl and ($C_{0-3}$-alkanedyl-$C_{3-7}$-cycloalkyl, whereby in at least one of radicals $R^5$ and $R^{5'}$, a C atom can be exchanged for O, S, SO, $SO_2$, NH, N—$C_{1-3}$-alkyl or N—$C_{1-3}$-alkanoyl, whereby a ring member in the cycloalkyl ring can be ring-N or ring-O if the cycloalkyl ring is five-membered, or one or two ring members in the cycloalkyl ring in each case can be one or two ring-N and/or ring-O atoms if the cycloalkyl ring is six- or seven-membered, whereby the ring-N atoms can be substituted with at least one radical that is selected from the group consisting of $C_{1-3}$-alkyl, $C_{1-3}$-alkanoyl, ($C_{0-3}$-alkanediyl-aryl) and ($C_{0-3}$-alkanediyl-heteroaryl), whereby the heteroaryl group can be five- or six-membered and can contain one or two heteroatoms, selected from the group consisting of N, S and O, whereby at least one of the alkyl and cycloalkyl radicals of $R^5$ and $R^{5'}$ is optionally substituted with up to two radicals selected from the group consisting of $CF_3$, $C_2F_5$, OH, O—$C_{1-3}$-alkyl, $NH_2$, NH—$C_{1-3}$-alkyl, NH—$C_{1-3}$-alkanoyl, N($C_{1-3}$-alkyl)$_2$, N($C_{1-3}$-alkyl)($C_{1-3}$-alkanoyl), COOH, $CONH_2$ and COO—$C_{1-3}$-alkyl, and at least one of the aryl and heteroaryl groups of $R^5$ and $R^{5'}$ is optionally substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or at least one of the alkyl, cycloalkyl, aryl and/or heteroaryl radicals of $R^5$ and $R^{5'}$ can carry an anellated methanediylbisoxy group or ethane-1,2-diylbisoxy group, or, whereby $R^5$ and $R^{5'}$ together with the amide-N-atom of B form a five- to seven-membered, saturated or unsaturated heterocyclic ring, which opptionally contains another N or O or S atom and which is opptionally substituted with $C_{1-4}$-alkyl, ($C_{0-2}$-alkanediyl-$C_{1-4}$-alkoxy), $C_{1-4}$-alkoxycarbonyl, aminocarbonyl or aryl, $R^6$ stands for a radical that is selected from the group consisting of ($C_{0-3}$-alkanediyl-aryl) and ($C_{0-3}$-alkanediyl-heteroaryl), whereby the heteroaryl group is five- or six-membered and contains one or two heteroatoms selected from the group consisting of N, S and O, and whereby at least one of the aryl or heteroaryl groups is optionally substituted with up to two radicals indepedently of one another selected from the group consisting of F, Cl, Br, $CH_3$, $C_2H_5$, OH, $OCH_3$, $OC_2H_5$, $NO_2$, $N(CH_3)_2$, $CF_3$, $C_2F_5$, and $SO_2NH_2$, or at least one of the aryl or heteroaryl groups can also carry an anellated methanediylbisoxy group or ethane-1,2-diylbisoxy group.

2. A benzimidazole derivative according to claim 1, wherein $R^1$ stands for phenyl opptionally substituted with up to two radicals, independently of one another selected from the group consisting of F, Cl, Br, $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$, H, $OR^4$, $OCOR^4$, $OCONHR^4$, $COR^4$, $C(NOH)R^4$, CN, COOH, $COOR^4$, $CONH_2$, $CON^4R^{4'}$, $CONHR^4$, CONHOH, $SR^4$, $SOR^4$, $SO_2R^4$, $SO_2NH_2$, $SO_2NHR^4$, $SO_2NR^4R^{4'}$, $NO_2$, $NH_2$, $NHR^4$, $NHCONHR^4$ and $R^4$.

3. A benzimidazole derivatives according to claim 1, wherein $R^3$ is a radical that is selected from the group consisting of hydrogen, F, Cl, Br, $CH_3$, $C_2H_5$, $CF_3$, $C_2F_5$, OH, $OR^4$, $NHSO_2R^6$ and $NHCOR^4$.

4. A benzimidazole derivative according to claim 1, wherein B stands for a radical that is selected from the group consisting of COOH, $COOR^5$, $CONH_2$, $CONHR^5$ and $CONR^5NR^{5'}$.

5. A benzimidazole derivative according to claim 1, wherein Y stands for O.

6. A benzimidazole derivative according to claim 1, wherein $R^6$ stands for a phenyl or heteroaryl group, whereby the heteroaryl group, is five- or six-membered and contains one or two heteroatoms selected from the group consisting of N, S and O.

7. A benzimidazole derivative of general formula I according to claim 1, in which:

$R^1$ means a phenyl group, which is optionally substituted with up to two radicals, independently of one another selected from the group consisting of F, Cl, Br, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$, OH, OR$^4$, OCOR$^4$, OCONHR$^4$, COR$^4$, C(NOH)R$^4$, CN, COOH, COOR$^4$, CONH$_2$, CONR$^4$R$^{4'}$, CONHR$^4$, CONHOH, SR$^4$, SOR$^4$, SO$_2$R$^4$, SO$_2$NH$_2$, SO$_2$NHR$^4$, SO$_2$NR$^4$R$^{4'}$, NO$_2$, NH$_2$, NHR$^4$, NR$^4$R$^{4'}$, NHCONHR$^4$ and R$^4$, whereby two substituents at R$^1$ are linked to one another in such a way that they jointly form a methanediylbisoxy, ethane-1,2-diylbisoxy, propane-1,3-diyl or butane-1,4-diyl group if they are in ortho-position to one another, Z means NH, NR$^{2'}$ or O, R$^2$ and R$^{2'}$, independently of one another, mean a radical that is selected from the group consisting of C$_{1-4}$-perfluoroalkyl, C$_{1-6}$-alkyl, (C$_{0-3}$-alkanediyl-aryl) and (C$_{0-3}$-alkanediyl-heteroaryl), whereby the heteroaryl group is five- or six-membered and contains one or two heteroatoms selected from the group consisting of N, S and O, and whereby the aryl and heteroaryl group in each case is optionally substituted with up to two radicals selected from the group consisting of F, Cl, Br, CH$_3$, C$_2$H$_5$, OH, OCH$_3$, OC$_2$H$_5$, NO$_2$, CF$_3$, C$_2$F$_5$ and SO$_2$NH$_2$, or if Z is NR$^{2'}$, R$^2$ and R$^{2'}$ together with Z form a five- to seven-membered heterocyclic ring, whereby the heterocyclic ring contain another N, O or S atom and is optionally substituted with a radical that is selected from the group consisting of C$_{1-4}$-alkyl, (C$_{0-3}$-alkanediyl-C$_{1-3}$-alkoxy), C$_{1-4}$-alkanoyl, C$_{1-4}$-alkoxycarbonyl, aminocarbonyl and aryl, R$^3$ means hydrogen, A means straight-chain or branched alkanediyl with up to 8 C atoms, B means a radical that is selected from the group consisting of COOH, COOR$^5$, CONH$_2$, CONHR$^5$ and CONR$^5$R$^{5'}$, in each case bonded to a C atom of group A, Y means O, R$^4$ and R$^{4'}$, independently of one another, in each case mean a radical that is selected from the group consisting of CF$_3$, C$_2$F$_5$, C$_{1-4}$-alkyl, C$_{2-4}$-alkenyl, C$_{2-3}$-alkinyl and (C$_{0-3}$-alkanediyl-C$_{3-7}$-cycloalkyl), whereby the alkyl radical is optionally substituted with a radical that is selected from the group consisting of OH, OCH$_3$ and SCH$_3$, R$^5$ and R$^{5'}$, independently of one another, in each case mean a radical that is selected from the group consisting of C$_{1-6}$-alkyl, C$_{2-6}$-alkenyl, C$_{2-6}$-alkinyl, (C$_{0-3}$-alkanediyl-C$_{3-7}$-cycloalkyl), (C$_{0-3}$-alkanediyl-phenyl) and (C$_{0-3}$-alkanediyl-heteroaryl), whereby the heteroaryl group is five- or six-membered and contains one or two heteroatoms, selected from the group consisting of N, S and O, whereby all previously mentioned alkyl and cycloalkyl radicals are optionally substituted optionally with a radical that is selected from the group consisting of CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, N(C$_{1-3}$-alkyl)(C$_{1-3}$-alkanoyl), COOH, CONH$_2$ and COO—C$_{1-3}$-alkyl, and all previously mentioned phenyl and heteroaryl groups are optionally substituted with up to two radicals selected from the group consisting of F, Cl, Br, CH$_3$, C$_2$H$_5$, OH, OCH$_3$, OC$_2$H$_5$, NO$_2$, N(CH$_3$)$_2$, CF$_3$, C$_2$F$_5$ and SO$_2$NH$_2$, and/or also can carry an anellated methanediylbisoxy group or ethane-1,2-diylbisoxy group, or R$^5$ and R$^{5'}$ together with the amide-N atom of B form a five- to seven-membered, saturated or unsaturated heterocyclic ring, which can contain another N or O or S atom and which can be substituted with C$_{1-4}$-alkyl, (C$_{0-2}$-alkanediyl-C$_{1-4}$-alkoxy), C$_{1-4}$-alkoxycarbonyl, aminocarbonyl or phenyl.

8. A benzimidazole derivative according to claim 7, wherein R$^5$ and R$^{5'}$ in each case independently of one another stand for a radical that is selected from the group consisting of C$_{1-6}$-alkyl, C$_{2-6}$-alkenyl, C$_{2-6}$-alkinyl, (C$_{0-3}$-alkanediyl-C$_{3-7}$-cycloalkyl), (C$_{0-3}$-alkanediyl-aryl) and (C$_{0-3}$-alkanediyl-heteroaryl), whereby aryl stands for phenyl and the alkyl and cycloalkyl radicals are substituted with a radical that is selected from the group consisting of CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, (N(C$_{1-3}$-alkyl) (C$_{1-3}$-alkanoyl), COOH, CONH$_2$, and COO—C$_{1-3}$-alkyl.

9. A benzimidazole derivative according to claim 7, wherein aryl in R$^1$ stands for phenyl (C$_6$H$_5$—) or p-methyl-phenyl (p-CH$_3$—C$_6$H$_4$—).

10. A benzimidazole derivative according to claim 7, wherein R$^2$ stands for C$_{1-3}$-alkyl, phenyl, methylphenylene, benzyl or heteroaryl.

11. A pharmaceutical preparation comprising at least one benzimidazole derivative of general formula I according to claim 1 and at least one pharmaceutically compatible vehicle.

12. A benzimidazole derivative according to claim 1 selected from the group consisting of:

6-[[2-(Morpholin-4-yl)-1-phenyl-1H-benzimidazol-6-yl]oxy]hexanoic acid methyl ester, 6-[[2-(Piperidin-1-yl)-1-phenyl-1H-benzimidazol-6-yl]oxy]hexanoic acid methyl ester, 6-[[1-(4-Methylphenyl)-2-(morpholin-4-yl)-1H-benzimidazol-6-yl]oxy]hexanoic acid methyl ester, 6-[[1-(4-Methylphenyl)-2-(piperidin-1-yl)-1H-benzimidazol-6-yl]oxy]hexanoic acid methyl ester, N-(3-Methoxypropyl)-6-[[2-(morpholin-4-yl)-1-phenyl-1H-benzimidazol-6-yl]oxy]hexanamide, N-(3-Methoxypropyl)-6-[[2-(piperidin-1-yl)-1-phenyl-1H-benzimidazol-6-yl]oxy]hexanamide, 6-[[2-Methoxy-1-phenyl-1H-benzimidazol-6-yl]oxy]hexanoic acid methyl ester, 6-[[2-Methoxy-1-phenyl-1H-benzimidazol-6-yl]oxy]hexanoic acid, 6-[[2-Ethoxy-1-phenyl-1H-benzimidazol-6-yl]oxy]hexanoic acid methyl ester, 6-[[2-Ethoxy-1-phenyl-1H-benzimidazol-6-yl]oxy]hexanoic acid, 6-[[1-Phenyl-2-phenylamino-1H-benzimidazol-6-yl]oxy]hexanoic acid methyl ester, 6-[[1-Phenyl-2-phenylamino-1H-benzimidazol-6-yl]oxy]hexanoic acid, 6-[[1-(4-Methylphenyl)-2-phenylamino-1H-benzimidazol-6-yl]oxy]hexanoic acid methyl ester, 6-[[1-Phenyl-2-propylamino-1H-benzimidazol-6-yl]oxy]hexanoic acid methyl ester, 6-[[1-Phenyl-2-propylamino-1H-benzimidazol-6-yl]oxy]hexanoic acid, 6-[[2-(N-Methyl-N-propyl)amino-1-phenyl-1H-benzimidazol-6-yl]oxy]hexanoic acid methyl ester, and 6-[[1-(4-Methylphenyl)-2-phenyloxy-1H-benzimidazol-6-yl]oxy]hexanoic acid.

13. A method of treating inflammatory or allergic diseases comprising administering an effective amount of a benzimidazole derivative of general formula I according to claim 1 to a patient in need thereof.

14. The method of claim 13 wherein the disease is stroke.

* * * * *